United States Patent
Ganatra et al.

(10) Patent No.: US 10,227,713 B2
(45) Date of Patent: *Mar. 12, 2019

(54) METHODS OF ORIENTING MULTIFILAMENT YARN AND MONOFILAMENTS OF POLY-4-HYDROXYBUTYRATE AND COPOLYMERS THEREOF

(71) Applicant: Tepha, Inc., Lexington, MA (US)

(72) Inventors: Amit Ganatra, Attleboro, MA (US); Fabio Felix, Foxborough, MA (US); Bhavin Shah, Lowell, MA (US); Matthew Bernasconi, Norwood, MA (US); Said Rizk, Windham, NH (US); David P. Martin, Arlington, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/368,922

(22) Filed: Dec. 5, 2016

(65) Prior Publication Data

US 2017/0081784 A1 Mar. 23, 2017

Related U.S. Application Data

(63) Continuation of application No. 14/964,985, filed on Dec. 10, 2015, now Pat. No. 9,555,155.

(60) Provisional application No. 62/090,398, filed on Dec. 11, 2014, provisional application No. 62/162,232, filed on May 15, 2015.

(51) Int. Cl.
| | |
|---|---|
| *A61K 9/00* | (2006.01) |
| *D01F 6/62* | (2006.01) |
| *A61L 17/10* | (2006.01) |
| *A61L 31/06* | (2006.01) |
| *A61L 31/14* | (2006.01) |
| *B29C 55/00* | (2006.01) |
| *D01F 8/14* | (2006.01) |
| *D01D 5/08* | (2006.01) |
| *D02G 3/04* | (2006.01) |
| *B29K 73/00* | (2006.01) |
| *B29L 31/00* | (2006.01) |
| *B29K 673/00* | (2006.01) |

(52) U.S. Cl.
CPC ............ *D01F 6/625* (2013.01); *A61L 17/105* (2013.01); *A61L 31/06* (2013.01); *A61L 31/148* (2013.01); *B29C 55/005* (2013.01); *D01D 5/08* (2013.01); *D01F 8/14* (2013.01); *D02G 3/04* (2013.01); *B29K 2073/00* (2013.01); *B29K 2673/00* (2013.01); *B29L 2031/731* (2013.01); *D10B 2331/04* (2013.01); *D10B 2331/041* (2013.01); *D10B 2401/063* (2013.01); *D10B 2509/04* (2013.01); *D10B 2509/08* (2013.01)

(58) Field of Classification Search
CPC ...................................................... D01F 6/625
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 3,982,543 A | 9/1976 | Schmitt |
| 4,031,894 A | 6/1977 | Urquhart |
| RE30,170 E | 12/1979 | Goodman |
| 4,201,211 A | 5/1980 | Chandrasekaran |
| 4,205,399 A | 6/1980 | Shalaby |
| 4,266,592 A | 8/1981 | Chandrasekaran |
| 4,314,557 A | 2/1982 | Chandrasekaran |

(Continued)

FOREIGN PATENT DOCUMENTS

| | | |
|---|---|---|
| CA | 2307637 | 5/1999 |
| CA | 2259098 | 7/1999 |

(Continued)

OTHER PUBLICATIONS

Abate, et al., "Separation and structural characterizations of cyclic and open chain oligomers produced in the partial pyrolysis of microbial poly(hydroxydryates)", Macromolecules, 28(23):7911-1916 (1995).

Abate,et al., "Thermal Degradatuion of Microbial Poly(4-hydrixbutyrate)", Macromolecules, 27:332-336 (1994).

Agostini, et al., "Synthesis and Characterization of Poly-β-Hydroxybutyrate. I. Synthesis of Crystalline DL Poly-β-Hydroxybutyrate from DL-β-Butyrolactone," Polym. Sci., Part A 1 9:2775-87 (1971).

Anderson, et al., "Occurrence, Metabolism, metabolic Role, and Industrial Uses of Bacterial Polyhydroxyalkanoates," Microbiological Reviews pp. 450-472 (1990).

(Continued)

*Primary Examiner* — Paul W Dickinson
(74) *Attorney, Agent, or Firm* — Pabst Patent Group LLP

(57) ABSTRACT

Resorbable multifilament yarns and monofilament fibers including poly-4-hydroxybutyrate and copolymers thereof with high tenacity or high tensile strength have been developed. The yarns and fibers are produced by cold drawing the multifilament yarns and monofilament fibers before hot drawing the yarns and fibers under tension at temperatures above the melt temperature of the polymer or copolymer. These yarns and fibers have prolonged strength retention in vivo making them suitable for soft tissue repairs where high strength and strength retention is required. The multifilament yarns have tenacities higher than 8.1 grams per denier, and in vivo, retain at least 65% of their initial strength at 2 weeks. The monofilament fibers retain at least 50% of their initial strength at 4 weeks in vivo. The monofilament fibers have tensile strengths higher than 500 MPa. These yarns and fibers may be used to make various medical devices for various applications.

38 Claims, No Drawings

(56) References Cited

U.S. PATENT DOCUMENTS

| | | |
|---|---|---|
| 4,379,454 A | 4/1983 | Campbell |
| 4,435,180 A | 3/1984 | Leeper |
| 4,537,738 A | 8/1985 | Holmes |
| 4,559,222 A | 12/1985 | Enscore |
| 4,573,995 A | 3/1986 | Chen |
| 4,588,580 A | 5/1986 | Gale |
| 4,603,070 A | 7/1986 | Steel |
| 4,645,502 A | 2/1987 | Gale |
| 4,648,978 A | 3/1987 | Makinen |
| 4,664,655 A | 5/1987 | Orentreich |
| 4,704,282 A | 11/1987 | Campbell |
| 4,711,241 A | 12/1987 | Lehmann |
| 4,743,257 A | 5/1988 | Tormala |
| 4,758,234 A | 7/1988 | Orentreich |
| 4,788,062 A | 11/1988 | Gale |
| 4,792,336 A | 12/1988 | Hlavacek |
| 4,816,258 A | 3/1989 | Nedberge |
| 4,826,493 A | 5/1989 | Martini |
| 4,849,226 A | 7/1989 | Gale |
| 4,853,226 A | 8/1989 | Machida |
| 4,856,188 A | 8/1989 | Sibalis |
| 4,876,331 A | 10/1989 | Doi |
| 4,880,592 A | 11/1989 | Martini |
| 4,908,027 A | 3/1990 | Enscore |
| 4,910,145 A | 3/1990 | Holmes |
| 4,938,763 A | 7/1990 | Dunn |
| 4,943,435 A | 7/1990 | Baker |
| 4,968,317 A | 11/1990 | Tormala |
| 5,002,067 A | 3/1991 | Berthelsen |
| 5,026,381 A | 6/1991 | Li |
| 5,032,638 A | 7/1991 | Wang |
| 5,041,100 A | 8/1991 | Rowland |
| 5,085,629 A | 2/1992 | Goldberg |
| 5,124,371 A | 6/1992 | Tokiwa |
| 5,128,144 A | 7/1992 | KorsatkoWabnegg |
| 5,171,308 A | 12/1992 | Gallagher |
| 5,204,382 A | 4/1993 | Wallace |
| 5,236,431 A | 8/1993 | Gogolewski |
| 5,245,023 A | 9/1993 | Peoples |
| 5,250,430 A | 10/1993 | Peoples |
| 5,271,961 A | 12/1993 | Mathiowitz |
| 5,278,201 A | 1/1994 | Dunn |
| 5,278,202 A | 1/1994 | Dunn |
| 5,278,256 A | 1/1994 | Bellis |
| 5,288,516 A | 2/1994 | Anderson |
| 5,292,860 A | 3/1994 | Shiotani |
| 5,306,286 A | 4/1994 | Stack |
| 5,334,698 A | 8/1994 | Witholt |
| 5,412,067 A | 5/1995 | Shinoda |
| 5,443,458 A | 8/1995 | Eury |
| 5,468,253 A | 11/1995 | Bezwada |
| 5,480,394 A | 1/1996 | Ishikawa |
| 5,480,794 A | 1/1996 | Peoples |
| 5,489,470 A | 2/1996 | Noda |
| 5,502,116 A | 3/1996 | Noda |
| 5,502,158 A | 3/1996 | Sinclair |
| 5,512,669 A | 4/1996 | Peoples |
| 5,516,565 A | 5/1996 | Matsumoto |
| 5,516,883 A | 5/1996 | Hori |
| 5,534,432 A | 7/1996 | Peoples |
| 5,536,564 A | 7/1996 | Noda |
| 5,550,173 A | 8/1996 | Hammond |
| 5,551,954 A | 9/1996 | Buscemi |
| 5,563,239 A | 10/1996 | Hubbs |
| 5,584,885 A | 12/1996 | Beckel |
| 5,614,576 A | 3/1997 | Rutherford |
| 5,625,030 A | 4/1997 | Williams |
| 5,629,077 A | 5/1997 | Turnlund |
| 5,635,215 A | 6/1997 | Boschetti |
| 5,646,217 A | 7/1997 | Hammond |
| 5,648,100 A | 7/1997 | Boschetti |
| 5,670,161 A | 9/1997 | Healy |
| 5,703,160 A | 12/1997 | Dehennua |
| 5,705,187 A | 1/1998 | Unger |
| 5,709,854 A | 1/1998 | GriffithCima |
| 5,711,933 A | 1/1998 | Bichon |
| 5,728,752 A | 3/1998 | Scopelianos |
| 5,735,863 A | 4/1998 | DellaValle |
| 5,753,364 A | 5/1998 | Rutherford |
| 5,753,708 A | 5/1998 | Koehler |
| 5,789,536 A | 8/1998 | Liggat |
| 5,811,272 A | 9/1998 | Snell |
| 5,814,071 A | 9/1998 | McDevitt |
| 5,814,599 A | 9/1998 | Mitragotri |
| 5,824,333 A | 10/1998 | Scopelianos |
| 5,824,751 A | 10/1998 | Hori |
| 5,834,582 A | 11/1998 | Sinclair |
| 5,840,331 A | 11/1998 | VanCauter |
| 5,842,477 A | 12/1998 | Naughton |
| 5,855,619 A | 1/1999 | Caplan |
| 5,874,040 A | 2/1999 | Liggat |
| 5,876,452 A | 3/1999 | Athanasiou |
| 5,876,455 A | 3/1999 | Harwin |
| 5,879,322 A | 3/1999 | Lattin |
| 5,917,002 A | 6/1999 | Doi |
| 5,919,478 A | 7/1999 | Landrau |
| 5,935,506 A | 8/1999 | Schmitz |
| 5,990,162 A | 11/1999 | Scharf |
| 5,994,478 A | 11/1999 | Asrar |
| 6,056,970 A | 5/2000 | Greenawalt |
| 6,103,255 A | 8/2000 | Levene |
| 6,119,567 A | 9/2000 | Schindler |
| 6,162,537 A | 12/2000 | Martin |
| 6,214,387 B1 | 4/2001 | Berde |
| 6,245,537 B1 | 6/2001 | Williams |
| 6,316,262 B1 | 11/2001 | Huisman |
| 6,323,010 B1 | 11/2001 | Skraly |
| 6,454,811 B1 | 9/2002 | Sherwood |
| 6,514,515 B1 | 2/2003 | Williams |
| 6,548,546 B2 | 4/2003 | Walker |
| 6,548,569 B1 | 4/2003 | Williams |
| 6,555,123 B2 | 4/2003 | Williams |
| 6,600,010 B2 | 7/2003 | Mao |
| 6,610,764 B1 | 8/2003 | Martin |
| 6,623,748 B2 | 9/2003 | Clokie |
| 6,623,749 B2 | 9/2003 | Williams |
| 6,645,622 B2 | 11/2003 | Yamane |
| 6,656,489 B1 | 12/2003 | Mahmood |
| 6,680,046 B1 | 1/2004 | Boschetti |
| 6,770,356 B2 | 8/2004 | ODonnell |
| 6,828,357 B1 | 12/2004 | Martin |
| 6,838,492 B2 | 1/2005 | Williams |
| 6,838,493 B2 | 1/2005 | Williams |
| 6,867,247 B2 | 3/2005 | Williams |
| 6,878,758 B2 | 4/2005 | Signer |
| 7,179,883 B2 | 2/2007 | Williams |
| 7,244,442 B2 | 7/2007 | Williams |
| 7,268,205 B2 | 9/2007 | Williams |
| 7,553,923 B2 | 6/2009 | Williams |
| 7,618,448 B2 | 11/2009 | Schmitz |
| 7,641,825 B2 | 1/2010 | Rizk |
| 8,016,883 B2 | 9/2011 | Coleman |
| 8,034,270 B2 | 10/2011 | Martin |
| 8,084,125 B2 | 12/2011 | Rizk |
| 8,231,889 B2 | 7/2012 | Williams |
| 8,287,909 B2 | 10/2012 | Martin |
| 8,431,060 B2 | 4/2013 | Huang |
| 8,747,468 B2 | 6/2014 | Martin |
| 8,758,657 B2 | 6/2014 | Martin |
| 2002/0028243 A1 | 3/2002 | Masters |
| 2002/0136848 A1* | 9/2002 | Yoshii .................. C08J 3/28 428/35.7 |
| 2002/0156150 A1 | 10/2002 | Williams |
| 2002/0173558 A1 | 11/2002 | Williams |
| 2003/0091803 A1 | 5/2003 | Bond |
| 2003/0185896 A1 | 10/2003 | Buiser |
| 2003/0211131 A1 | 11/2003 | Martin |
| 2004/0220355 A1 | 11/2004 | Whitehouse |
| 2004/0234576 A1* | 11/2004 | Martin .................. A61F 2/0063 424/426 |
| 2005/0107505 A1 | 5/2005 | Shinoda |
| 2005/0158542 A1 | 7/2005 | Iwata |
| 2005/0267516 A1 | 12/2005 | Soleimani |
| 2006/0058470 A1 | 3/2006 | Rizk |

(56) References Cited

U.S. PATENT DOCUMENTS

| | | |
|---|---|---|
| 2009/0012604 A1 | 1/2009 | Schmitz |
| 2009/0112259 A1 | 4/2009 | DAgostino |
| 2009/0162276 A1 | 6/2009 | Martin |
| 2010/0057123 A1 | 3/2010 | DAgostino |
| 2011/0236974 A1 | 9/2011 | Ogle |
| 2013/0218253 A1 | 8/2013 | Kaufmann |
| 2014/0277572 A1 | 9/2014 | Martin |

FOREIGN PATENT DOCUMENTS

| | | |
|---|---|---|
| CA | 2298421 | 2/2000 |
| CN | 101144196 | 3/2008 |
| DE | 3937649 | 5/1991 |
| EP | 0258781 | 3/1988 |
| EP | 0344704 | 12/1989 |
| EP | 0349505 | 3/1990 |
| EP | 0423484 | 4/1991 |
| EP | 0429403 | 5/1991 |
| EP | 0432443 | 5/1991 |
| EP | 0452111 | 10/1991 |
| EP | 0507554 | 10/1992 |
| EP | 0601885 | 6/1994 |
| EP | 0628586 | 12/1994 |
| EP | 0754467 | 1/1997 |
| EP | 1130043 | 9/2001 |
| EP | 1266984 | 12/2002 |
| EP | 2505213 | 10/2012 |
| GB | 2166354 | 5/1986 |
| JP | 62209144 | 9/1987 |
| JP | 03187386 | 8/1991 |
| JP | 04292619 | 10/1992 |
| JP | 04326932 | 11/1992 |
| JP | 05023189 | 2/1993 |
| JP | 05194141 | 11/1993 |
| JP | 06264306 | 9/1994 |
| JP | 06336523 | 12/1994 |
| JP | 07275344 | 10/1995 |
| JP | 08089264 | 4/1996 |
| JP | 08218216 | 8/1996 |
| JP | 09098793 | 4/1997 |
| JP | 09507091 | 7/1997 |
| JP | 00220032 | 8/2002 |
| WO | 9218164 | 10/1992 |
| WO | 9305824 | 4/1993 |
| WO | 9320134 | 10/1993 |
| WO | 9402184 | 2/1994 |
| WO | 9406886 | 3/1994 |
| WO | 9503356 | 2/1995 |
| WO | 9517216 | 6/1995 |
| WO | 9520614 | 8/1995 |
| WO | 9520615 | 8/1995 |
| WO | 9520621 | 8/1995 |
| WO | 9523249 | 8/1995 |
| WO | 9523250 | 8/1995 |
| WO | 9533874 | 12/1995 |
| WO | 9600263 | 1/1996 |
| WO | 9608535 | 3/1996 |
| WO | 9618420 | 6/1996 |
| WO | 9621427 | 7/1996 |
| WO | 9640304 | 12/1996 |
| WO | 9704036 | 2/1997 |
| WO | 9707153 | 2/1997 |
| WO | 9804292 | 2/1997 |
| WO | 9715681 | 5/1997 |
| WO | 9730042 | 8/1997 |
| WO | 9839453 | 9/1998 |
| WO | 9846028 | 10/1998 |
| WO | 9851812 | 11/1998 |
| WO | 9911196 | 3/1999 |
| WO | 9914313 | 3/1999 |
| WO | 9932536 | 7/1999 |
| WO | 9935192 | 7/1999 |
| WO | 0051662 | 9/2000 |
| WO | 0056378 | 9/2000 |
| WO | 0110421 | 2/2001 |
| WO | 0115671 | 3/2001 |
| WO | 0119361 | 3/2001 |
| WO | 02085963 | 10/2002 |
| WO | 2004101002 | 11/2004 |
| WO | 2006015276 | 2/2006 |
| WO | 20070922417 | 8/2007 |
| WO | 2009085823 | 7/2009 |
| WO | 2011106205 | 9/2011 |
| WO | 2011119742 | 9/2011 |
| WO | 2011159784 | 12/2011 |
| WO | 2012064526 | 5/2012 |
| WO | 2015006596 | 1/2015 |

OTHER PUBLICATIONS

Bandiera, et al., "Effect of sodium sulfonate groups on the ionic conductivity of a copolyester of thiodipropionic acid", Eur. Pol. J., 33:1679-1683 (1997).

Blight, "Miracles and molecules—progress in spinal cord repair," Nat. Neurosci. 5:1051-4 (2002).

Boeree, et al., "Development of a degradable composite for orthopaedic use: mechanical evaluation of an hydroxyapatite-polyhydroxybutyrate composite material", Biomaterials, 14 (10):793-6 (1993).

Braunegg, et al., "Polyhydroxyalkanoates, biopolyesters from renewable resources: physiological and engineering aspects," J. Biotech. 65: 127-161 (1998).

Breuer, et al., "Tissue Engineering Lamb Heart Valve Leaflets," Biotechnology & Bioengineering 50:562-67 (1996).

Campbell & Bailey, "Mechanical properties of suture materials in vitro and after in vivo implantation in horses," Vet. Surg. 21(5):355-61 (1992).

Dayton, et al., "Use of an absorbable mesh to repair contaminated abdominal-wall defects" Archives of Surgery 121(8): 954-960 (1986).

Ferreira, et al., "Films of Poly(L—Lactic Acid)/Poly(Hydroxybutyrate-co-Hydroxyvalerate) Blends:In vitro Degradation", Materials Research, 4(1):34-42 (2001).

Freed, et al., "Biodegradable polymer scaffolds for tissue engineering", Biotechnology, 12:689-693 (1994).

Gordeyev, et al., "Processing of gel-spun poly($^2$-hydroxybutyrate) fibers", Journal of Applied Polymer Science, 81:2260-2264 (2001).

Holmes, et al., "Applcations of PHB a microbially produced biodegradable thermoplastic," Phys Technol 16:32-36 (1985).

Hori, et al., "Chemical synthesis of a high molecular weight poly(3-hydroxybutyrate-co-4-hydroxybutyrate)" Polymer 36(24): 4703-4705 (1995).

Hori, et al., "Ring-Opening Copolymerization of Optically Active β-Butyrolactone with Several Lactones Catalyzed by Distannoxane Complexes: Synthesis of New Biodegradable Polyesters," Macromolecules 26:4388-90 (1993).

Hori, et al., "Ring-Opening Polymerization of Optically Active βButyrolactone Using Distannoxane Catalysts Synthesis of High Molecular Wright Poly(3-hydroxybutyrate)," Macromolecules 26:5533-34 (1993).

Houk, et al., "Why delta-valerolactone polymerizes and gamma-butyrolactone does not", J. Org. Chem., 73 (7):2674-8 (2008).

Martin and Williams, "Medical application of poly-4-hydroxybutyrate: A strong flexible absorbable biomaterial", Biochem. Eng. J., 16:97-105 (2003).

Moore, et al., "Chemosynthesis of bioresorbable poly(gamma-butyrolactone) by ring-opening polymerisation: a review", Biomaterials, 26:3771-82 (2005).

Odermatt, et al. MonoMax Suture: A new long-term absorbable monofilament suture made from poly-4-hydroxybutyrate, Int. J. Polymer Science, Article 216137, 12 pages (2012).

Rousselle, et al., "Structural requirement for cell adhesion to Kalinin (laminin-5)", J Biol Chem., 270(22(:13766-70 (1995).

Singha, et al., "Effects of fiber diameter distribution of nonwoven fabrics on its properties", Itl J Textile Sci., 1(1):7-14 (2012).

Williams, et al. Poly-4-hydrobutyrate (P4HB): a new generation of resorbable medical devices for tissue repair and regeneration, Biomed. Tech. 58(5):439-452 (2013).

(56) References Cited

OTHER PUBLICATIONS

Williams, et al., "Applications of PHA\s in medicine and pharmacy", Polyesters, III, 4:91-127 (2002).

* cited by examiner

METHODS OF ORIENTING MULTIFILAMENT YARN AND MONOFILAMENTS OF POLY-4-HYDROXYBUTYRATE AND COPOLYMERS THEREOF

CROSS-REFERENCE TO RELATED APPLICATIONS

This application is a continuation of U.S. application Ser. No. 14/964,985, filed Dec. 10, 2015, which claims benefit of U.S. Provisional Application No. 62/090,398, filed Dec. 11, 2014, and U.S. Provisional Application No. 62/162,232, filed May 15, 2015, the contents of which are incorporated by reference herein in their entirety.

FIELD OF THE INVENTION

The present invention generally relates to resorbable multifilament yarn and monofilament fibers of poly-4-hydroxybutyrate (P4HB) and copolymers, and improved methods for their production. The multifilament yarns have improved tenacity and the monofilaments have higher tensile strength, which allows a surgeon to use medical devices made from these yarns and monofilaments where high strength is essential. Furthermore, the resorbable yarns and monofilaments also have higher strength retention when implanted. The higher strength retention in vivo allows the yarns and monofilaments to provide temporary support for soft and hard tissue repair for longer periods than was previously possible. The improved methods of production of the multifilament yarns and monofilament fibers provide yarns and fibers with more consistent mechanical properties and higher strengths that are particularly important for use in medical devices and implants. Improved production and productivity is achieved by first orienting the multifilament yarns and monofilament fibers using a cold draw before hot drawing. Devices and implants made from the monofilament fibers, such as sutures and meshes, have more predictable strength retention profiles in vivo allowing the fibers to provide reliable temporary support for soft and hard tissue repair over prolonged periods.

BACKGROUND OF THE INVENTION

Multifilament products made from resorbable polymers, such as copolymers of glycolide and lactide, and monofilament products made from resorbable polymers, such as polydioxanone (PDO), are well known in the prior art, and widely used in wound closure and general surgery. However, these products undergo rapid loss of strength retention in vivo, which limits their application primarily to fast healing repairs, and repairs where prolonged strength retention is not necessary. For example, while a surgeon may use a resorbable multifilament suture to approximate soft tissue that is not under significant tension, a surgeon will generally not use a resorbable suture when loads on the suture can be very high and remain high for a prolonged period, such as in rotator cuff repairs. Instead, surgeons will typically use permanent sutures for rotator cuff repairs even though it would be desirable to use a suture that is completely resorbed once healing is complete. Similarly, a surgeon may use a resorbable monofilament suture or mesh to approximate soft tissue that is not under significant tension, but will generally not use a resorbable monofilament suture or mesh when loads on the device can be very high and remain high for a prolonged period, such as in hernia repair. Instead, surgeons will typically use permanent (polypropylene) meshes for hernia repairs even though it would be desirable to use devices that completely resorb after healing is complete.

Thus in the practice of surgery there currently exists a need for a resorbable multifilament yarn with a high tenacity and prolonged strength retention, and a resorbable monofilament fiber with high tensile strength and prolonged strength retention. These multifilament yarns and monofilament fibers would allow the surgeon to use resorbable devices instead of permanent devices when high strength is initially required, or when prolonged strength retention is necessary. For example, the multifilament yarn could be used to make multifilament sutures suitable for the repair of rotator cuffs and other ligaments and tendons, or multifilament mesh suitable for hernia repair or breast lift procedures. And the monofilament fiber could be used to make monofilament sutures suitable for face-lift procedures, or monofilament meshes suitable for hernia repair, breast reconstruction and mastopexy.

Resorbable multifilament yarns and monofilament fibers have previously been prepared from poly-4-hydroxybutyrate (P4HB). P4HB (TephaFLEX® biomaterial) is a strong, pliable thermoplastic polyester that, despite its biosynthetic route, has a relatively simple structure. Upon implantation, P4HB hydrolyzes to its monomer, and the monomer is metabolized via the Krebs cycle to carbon dioxide and water.

U.S. Pat. No. 8,287,909 to Martin et al. discloses medical devices containing melt-blown nonwovens of poly-4-hydroxybutyrate and copolymers thereof with average fiber diameters of 1 µm to 50 µm. WO 2011/159784 to Cahil et al. discloses medical devices containing dry spun nonwovens of P4HB and copolymers thereof, and continuous processing methods for their preparation.

Odermatt et al. MonoMax Suture: A new long-term absorbable monofilament suture made from poly-4-hydroxybutyrate, *Int. J. Polymer Science*, Article 216137, 12 pages (2012) disclose a monofilament suture made from P4HB, but does not disclose multifilament yarn or multifilament sutures made from P4HB. U.S. Pat. Nos. 7,641,825 and 8,084,125 to Rizk disclose non-curling sutures of P4HB that are made by relaxing and annealing P4HB monofilament. Rizk does not disclose P4HB multifilament yarn or sutures with high tenacity or prolonged strength retention. In both Odermatt and Rizk, improvement of handling properties is achieved by relaxing the P4HB monofilament suture fiber resulting in a fiber that is not highly oriented.

Williams, et al. Poly-4-hydroxybutyrate (P4HB): a new generation of resorbable medical devices for tissue repair and regeneration, *Biomed Tech.* 58(5):439-452 (2013) discloses monofilament and multifilament fibers of P4HB.

U.S. Pat. Nos. 8,034,270 and 8,758,657 to Martin et al. disclose monofilament and multifilament knitted meshes of P4HB produced by knitting monofilament and multifilament fibers of P4HB. P4HB multifilament with tenacity ranging from 3.1 to 4.1 grams per denier, denier per filament ranging from 10.3 to 33.8, and elongation to break from 58 to 114% is disclosed.

U.S. Pat. No. 8,747,468 to Martin discloses P4HB monofilament and multifilament fiber, coatings and spin finishes for these fibers, and medical devices made from P4HB monofilament and multifilament fibers. The P4HB multifilament fibers have tenacities ranging from 6.524 to 8.081 grams per denier, and denier per filament ranging from 1.98 to 2.27.

U.S. Pat. No. 8,016,883 to Coleman et al. discloses methods and devices for rotator cuff repair, including medical devices containing knitted meshes of P4HB and nonwovens made from P4HB multifilament fibers. A P4HB multifilament fiber with a tenacity of 6.04 grams per denier, and denier per filament of 4.4 is disclosed.

WO 2015/006596 to Rizk et al. discloses soft suture anchors and preparation of P4HB monofilament and P4HB multifilament.

US Patent Application No. 2010/0057123 to D'Agostino and Rizk, and US Patent Application No. 2009/0112259 to D'Agostino disclose recombinant expressed bioabsorbable polyhydroxyalkanoate monofilament and multifilament self-retaining sutures.

There is still a need for multifilament fibers with improved strength retention and a high tenacity, and monofilament fibers with improved tensile strength.

It is an object of the present invention to provide a resorbable multifilament yarn with high tenacity, and a resorbable monofilament fiber with high tensile strength.

It is another object of the present invention to provide a resorbable multifilament yarn and a resorbable monofilament fiber with prolonged strength retention.

It is still a further object of the present invention to provide a resorbable multifilament yarn with high knot strength, pliability, and a good drape, and a resorbable monofilament fiber with good knot strength and pliability.

It is yet another object of this invention to provide methods to produce resorbable multifilament yarn with high tenacity or prolonged strength retention, and resorbable monofilament fiber with improved productivity and with high strength or prolonged strength retention.

It is still another object of this invention to provide methods to prepare medical devices and implants from the resorbable multifilament yarns and monofilament fibers.

It is still yet another object of this invention to provide methods to implant devices made from resorbable multifilament yarns and monofilament fibers that have high tenacity and prolonged strength retention.

SUMMARY OF THE INVENTION

Resorbable multifilament yarns with high tenacity have been developed. The yarns are made using poly-4-hydroxybutyrate homopolymers or copolymers thereof or polymeric blends including poly-4-hydroxybutyrate homopolymers or copolymers thereof. The yarns have excellent drape, pliability, can be knit or woven into meshes with high burst strength, and braided to form, for example, high strength sutures with high knot strength and soft knot bundles.

The resorbable multifilament yarns have tenacities higher than 8.1 grams per denier, preferably higher than 8.5 grams per denier, and even more preferably, greater than 9 or 9.5 grams per denier. In some embodiments, the yarns have a tenacity greater than 8.1 grams per dernier but less than 12 grams per dernier. In this embodiment, the multifilament yarn preferably has a tenacity between 8.1 and 10.5 grams per denier.

The multifilament yarns have a denier per filament ranging from 1.7 to 9.0, and more preferably 1.7 to 6.5.

The yarns preferably have an average elongation to break of 10% to 70%, more preferably 10% to 40%, and even more preferably from 15% to 35%.

In a particularly preferred embodiment, the yarns have a tenacity greater than 8.1 grams, a denier per filament greater than 2.27, preferably 4 or greater, and an elongation at break between 10 and 30%.

The multifilament yarns also have prolonged strength in vivo. In a preferred embodiment, the multifilament yarns retain at least 65% of their initial strength at 2 weeks in vivo, more preferably at least 70%, and even more preferably at least 75%.

Methods are provided for manufacturing high tenacity yarns of P4HB and copolymers thereof, as well as yarns of P4HB and copolymers thereof with prolonged strength retention, and yarns with denier per filament ranging from 1.7 to 9.0, and more preferably 1.7 to 6.5. The ability to produce high tenacity yarns has been made possible by improvements to the spinning process as well as the orientation process.

The multifilament yarns can be used for soft tissue repairs where high strength is required and also needs to be maintained for a prolonged period. The yarns can be used to make various medical devices, for example, sutures, knitted and woven meshes, non-woven meshes, suture tapes and patches.

Methods to produce resorbable monofilament fibers with high strength and prolonged in vivo strength retention have also been developed. The fibers are made using poly-4-hydroxybutyrate homopolymers or copolymers thereof or polymeric blends including poly-4-hydroxybutyrate homopolymers or copolymers thereof. The fibers have excellent flexibility, and can be knit, braided or woven into meshes with high burst strength.

The resorbable monofilament P4HB fibers have tensile strengths higher than 500 MPa, preferably higher than 800 MPa, and more preferably higher than 900 MPa, 1,000 MPa, 1,100 MPa, 1,200 MPa, 1,300 MPa, or 1,400 MPa.

In a preferred embodiment, resorbable monofilament P4HB fibers with tensile strengths higher than 500 MPa, preferably higher than 800 MPa, and more preferably higher than 900 MPa, 1,000 MPa, 1,100 MPa, 1,200 MPa, 1,300 MPa, or 1,400 MPa, (but less than 1,500 MPa) have diameters ranging from USP suture sizes 10 to 12-0, preferably USP suture sizes 4 to 10-0, more preferably USP suture sizes 2 to 8-0, and even more preferably USP suture sizes 1 to 8-0.

The monofilament fibers preferably also have one or more of the following properties: (i) an elongation to break between 15% and 120%, and (ii) a Young's modulus less than 2 GPa. In a particularly preferred embodiment, the monofilament fibers have a tensile strength greater than 800 MPa or 850 MPa, and an elongation to break between 15% and 120%, more preferably between 15% and 70%, and even more preferably an average elongation at break between 15% and 35% or 40%.

In another preferred embodiment, the monofilament fibers have a tensile strength greater than 800 MPa or 850 MPa, an average elongation to break of 15% to 35% or 40%, and an average diameter from 150 µm to 180 µm.

In yet another preferred embodiment, the monofilament fibers have a minimum average knot pull tensile strength greater than 0.25 kgf or 0.68 kgf, or 0.95 kgf or 1.77 kgf.

The monofilament fibers also have prolonged strength in vivo. In a preferred embodiment, the monofilament fibers retain at least 50% of their initial strength at 4 weeks in vivo, and more preferably at least 60%.

Methods are provided for manufacturing high strength monofilament fibers of P4HB and copolymers thereof, as well as fibers of P4HB and copolymers thereof with prolonged strength retention, and fibers with tensile strength greater than 500 MPa or more preferably greater than 800 MPa or 850 MPa, and even more preferably greater than 900 MPa, 1,000 MPa, 1,100 MPa, 1,200 MPa, 1,300 MPa, or 1,400 MPa. The ability to produce high strength monofilament fibers has been made possible by improvements to the orientation process.

The monofilament fibers can be used for soft tissue repairs where high strength is required and also needs to be maintained for a prolonged period. The fibers can be used to make various medical devices and implants, for example, sutures, knitted and woven meshes, suture tapes, braids, and patches.

DETAILED DESCRIPTION OF THE INVENTION

I. Definitions

"Bioactive agent" is used herein to refer to therapeutic, prophylactic, and/or diagnostic agents. It includes without limitation physiologically or pharmacologically active substances that act locally or systemically in the body.

"Biocompatible" as generally used herein means the biological response to the material or device being appropriate for the device's intended application in vivo. Any metabolites of these materials should also be biocompatible.

"Blend" as generally used herein means a physical combination of different polymers or components, as opposed to a copolymer comprised of two or more different monomers.

"Breaking load" as generally used herein means the force just sufficient to break or rupture the yarn.

"Burst strength" as used herein is determined by test method ASTM D6797-02 "Standard test method for bursting strength of fabrics constant rate of extension (CRE) ball burst test," using a MTS Q-Test Elite universal testing machine or similar device. The testing fixture uses a ⅜ inch diameter ball.

"Cold draw" as generally used herein means drawing at a temperature below 50° C., more preferably below 45° C.

"Copolymers of poly-4-hydroxybutyrate" as generally used herein means any polymer of 4-hydroxybutyrate with one or more different hydroxy acid units.

"Denier" is a measure of the size of a fiber or yarn. The weight in grams of 9,000 meters of fiber or yarn is one denier.

"Diameter" as generally used herein is determined according to the US Pharmacopeia (USP) standard for diameter of surgical sutures (USP 861).

"Elongation to break" ("ETB") as used herein means the increase in length of a material that occurs when tension is applied to break the material. It is expressed as a percentage of the material's original length.

"Endotoxin content" as used herein refers to the amount of endotoxin present in a sample, and is determined by the limulus amebocyte lysate (LAL) assay (described by Gorbet et al. Biomaterials, 26:6811-6817 (2005)).

"Hot draw" as generally used herein means drawing at a temperature above the melt temperature of the polymer or copolymer.

"Knot-pull tensile strength" as used herein is determined using a universal mechanical tester according to the procedures described in the US Pharmacopeia (USP) standard for testing tensile properties of surgical sutures (USP 881).

"Line speed" as used herein means, unless otherwise stated, the speed of the yarn at the first godet or roller. It is measured as meters of yarn/minute.

"Molecular weight" as used herein, unless otherwise specified, refers to the weight average molecular weight ($M_w$), not the number average molecular weight ($M_n$), and is measured by GPC relative to polystyrene.

"Non-curling" as generally used herein means the tendency of a fiber to curve or form coils during handling.

"Orientation ratio" as used herein is the ratio of the output speed to the input speed of two godets (or rollers) used to orient the yarn. For example, the orientation ratio would be 3 if the output speed of the multifilament yarn or monofilament fiber is 6 meters per minute, and the input speed of the multifilament yarn or monofilament fiber is 2 meters per minute.

"Pliable fiber" as generally used herein refers to a fiber with reduced stiffness.

"Poly-4-hydroxybutyrate" as generally used herein means a homopolymer of 4-hydroxybutyrate units. It may be referred to herein as P4HB.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Strength retention" as generally used herein means the amount of time that a material maintains a particular mechanical property following implantation or exposure to a particular set of conditions. For example, if the stress required to break a multifilament yarn or monofilament fiber after one month is half of its original value then the multifilament yarn or monofilament fiber is said to have a 50% strength retention after one month.

"Retained breaking load" as generally used herein means the force just sufficient to break or rupture the yarn measured after a period of time, for example, after implantation in an animal for a certain number of hours, days, weeks or months. The retained breaking load may be expressed as a load, or alternatively as a percentage of its original value.

"Spin finishes" are lubricants and antistatic agents that are applied to textile fibers and yarns during production and processing.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails. The suture pullout strength may be converted and expressed as Newtons.

"Tenacity" means the strength of a yarn or a filament for its given size, and is measured as the grams of breaking force per denier unit of yarn or filament and expressed as grams per denier (gpd).

"Tensile strength" as used herein means the maximum stress that a material can withstand while being stretched or pulled before failing or breaking.

"USP Size" as used herein means the suture as defined by the United States Pharmacopeia. The USP Sizes can be 10, 9, 8, 7, 6, 5, 4, 3, 2, 1, 0, 2-0, 3-0, 4-0, 5-0, 6-0, 7-0, 8-0, 9-0, 10-0, 11-0 and 12-0.

"Yarn" as used herein means a continuous strand of textile fibers, or filaments. The yarn may be twisted, not twisted, or substantially parallel strands.

II. Compositions

An orientated and optionally relaxed yarn of P4HB homopolymer or copolymers thereof, or blends thereof, produced using the methods disclosed herein, has one or more of the following properties: (i) a tenacity between 8.1 and 12 grams per denier, more preferably between 8.2 and 12 grams per denier, and even more preferably between 8.5 and 12 grams per denier; (ii) denier per filament between 1.7 to 9.0, and even more preferably between 1.7 and 6.5; (iii) elongation to break of 10-30%; and in vivo strength retention greater than 65% at two weeks. In some embodiments, the multifilament yarns retain at least 70% of their initial strength, and even more preferably at least 75% at 2 weeks in vivo. In some embodiments, the yarns have a denier per filament greater than 4.0 and tenacity higher than 8.1, or a denier per filament greater than 4.0 and tenacity higher than 8.1. In some embodiments, the yarns have a tenacity greater than 8.1 but less than 12 grams per denier. In other embodiments, the yarns have a tenacity between 8.1 and 10.5 grams per denier.

All combinations of tenacity, denier per filament, elongation to break and in vivo strength retention that fall within the disclosed ranges are contemplated and included in this disclosure.

For example, the yarns disclosed herein can have a combination of the following properties:

(1) a tenacity between 8.1 and 12 grams per denier, more preferably between 8.2 and 12 grams per denier, and even more preferably between 8.5 and 12 grams per denier; (ii) denier per filament of 1.7 to 9.0, and even more preferably between 1.7 and 6.5; (iii) elongation to break of 10-30%; and (iv) an in vivo strength retention greater than 65% at two weeks;

(2) a tenacity between 8.1 and 12 grams per denier, an elongation to break of 10-30%, a denier per filament of 1.7 to 6.5 and an in vivo strength retention of greater than 65% at two weeks;

(3) a denier per filament greater than 4.0 and tenacity higher than 8.1, or a denier per filament greater than 4.0 and tenacity higher than 8.1, preferably between 8.1 and 10.5, an elongation to break of 10-30% and an in vivo strength retention of greater than 65% at two weeks.

An orientated and optionally relaxed and/or annealed monofilament of P4HB homopolymer or copolymers thereof, or blends thereof, produced using the methods disclosed herein, has one or more of the following properties (i) an elongation to break of less than 500%, more preferably less than 300%, and even more preferably less than 120%, but greater than 15%; (ii) a tensile strength greater than 500 MPa, more preferably at least 800 MPa or 850 MPa, and even more preferably at least 900 MPa, 1,000 MPa, 1,100 MPa, 1,200 MPa, 1,300 MPa, or 1,400 MPa, but less than 1,600 MPa; and (iii) a Young's modulus less than 2 GPa, more preferably less than 1 GPa, but greater than 70 MPa. In a preferred embodiment the oriented and optionally relaxed and/or annealed monofilament of P4HB homopolymer or copolymers thereof, or blends thereof, produced using the methods disclosed herein, has one or more of the following properties: (i) an elongation to break between 15% and 120%; break strength greater than 850 MPa; and a Young's modulus less than 2 GPa. In some embodiments, the monofilaments retain at least 15% of their initial strength, preferably at least 40% of their initial strength, more preferably at least 50% of their initial strength, and even more preferably at least 55% of their initial strength at 12 weeks in vivo. The monofilaments of P4HB homopolymer or copolymer thereof, or blends thereof, produced using the methods disclosed herein may optionally meet the requirements for diameter and knot-pull tensile strength of absorbable sutures defined by the United States Pharmacopoeia (USP). The sizes, minimum and maximum average diameters, and average minimum knot-pull tensile strengths (in kgf) defined by the USP standard are shown in Table 1. Thus, for example, a size 5-0 suture must have a minimum average diameter of 0.1 mm, a maximum average diameter of 0.149 mm, and a minimum average knot-pull tensile strength of 0.68 kgf. It will be apparent by inspection of Table 1 that the knot-pull tensile strength of an absorbable suture increases as the diameter of the suture increases. The values shown in Table 1 are determined according to procedures defined in the US Pharmacopeia.

TABLE 1

Knot-Pull Tensile Strengths Defined by the USP Standards for Different Absorbable Suture Sizes

| USP Suture Size | Average Min. Diameter (mm) | Average Max. Diameter (mm) | Knot-Pull Tensile Strength (Average Min. kgf) |
|---|---|---|---|
| 10-0 | 0.020 | 0.029 | 0.025* |
| 9-0 | 0.030 | 0.039 | 0.050* |
| 8-0 | 0.040 | 0.049 | 0.07 |
| 7-0 | 0.050 | 0.069 | 0.14 |
| 6-0 | 0.070 | 0.099 | 0.25 |
| 5-0 | 0.10 | 0.149 | 0.68 |
| 4-0 | 0.15 | 0.199 | 0.95 |
| 3-0 | 0.20 | 0.249 | 1.77 |
| 2-0 | 0.30 | 0.339 | 2.68 |
| 0 | 0.35 | 0.399 | 3.90 |
| 1 | 0.40 | 0.499 | 5.08 |
| 2 | 0.50 | 0.599 | 6.35 |
| 3 and 4 | 0.60 | 0.699 | 7.29 |

*The tensile strength of these sizes is measured by straight pull

In some embodiments, the monofilament fibers of P4HB homopolymer or copolymers thereof, or blends thereof, produced using the methods disclosed herein do not meet the US Pharmacopeia standard for average minimum knot-pull strength as shown in Table 1. In these cases, the monofilaments may still be referenced by the USP standard for knot-pull tensile strength, but as oversized monofilaments. For example, a monofilament of P4HB homopolymer may be prepared such that its diameter is sized up to 0.1 mm more than the USP standard in order to have the knot-pull tensile strength defined by the USP. In these instances the monofilament is said to meet the USP, but is oversized for diameter. Monofilaments of P4HB homopolymer or copolymers thereof, or blends thereof, produced using the methods disclosed herein may meet the USP standard for knot-strength shown in Table 1, but be oversized in diameter by up to 0.001, 0.01, 0.1 or 0.5 mm, but more preferably oversized by 0.0001 mm to 0.1 mm in diameter.

These combinations are provided for exemplary purposes only, and are not meant to be limiting.

The compositions also include mesh products made from the multifilament yarns and monofilament fibers disclosed herein. The meshes made from multifilament yarns have one or more of the following properties: (i) stretch by less than 30% of the scaffold's original length in any direction, (ii) a suture pullout strength of at least 1 Kgf, (iii) a burst strength of 0.1 to 100 Kg, (iv) a thickness of 0.1-5 mm and (v) an areal density of 5 to 800 g/m$^2$. In a particularly preferred embodiment, the mesh comprises P4HB multifilament fibers, and has an areal density of 5 to 800 g/m$^2$. The meshes made from P4HB monofilaments have one or more of the following properties: (i) a suture pullout strength of at least 1 Kgf, (ii) a burst strength of 0.1 to 100 Kg, (iii) a thickness of 0.05-5 mm, (iv) an areal density of 5 to 800 g/m$^2$, and (v) pore diameter of 5 µm to 5 mm. In a preferred embodiment, the monofilament meshes have one or more of the following properties: (i) a suture pullout strength of 1 Kgf to 20 Kgf, (ii) a burst strength of 1 to 50 Kg, more preferably 10 to 50

Kg, (iii) a thickness of 0.1 to 1 mm, (iv) areal density of 100 to 300 g/m$^2$, and (v) pore diameter 100 μm to 1 mm.

A. Polymers

The high tenacity resorbable yarns and high strength monofilaments include a poly-4-hydroxybutyrate (P4HB) homopolymer or a copolymer thereof. If desired, the P4HB polymers and copolymers thereof may be blended or mixed with other materials prior to preparing the high tenacity yarns. P4HB and its copolymers may be blended with other resorbable polymers.

In a preferred embodiment, the P4HB homopolymer and copolymers thereof used to prepare the high tenacity yarns and high strength monofilaments have a weight average molecular weight, Mw, within the range of 50 kDa to 1,200 kDa (by GPC relative to polystyrene) preferably between 100 kDa and 1000 kDa, and more preferably from 100 kDa to 600 kDa.

(i) P4HB Homopolymer and Copolymers

Copolymers of P4HB include 4-hydroxybutyrate copolymerized with another hydroxyacid, such as 3-hydroxybutyrate, and 4-hydroxybutyrate copolymerized with glycolic acid or lactic acid monomer.

P4HB homopolymer is not a natural product, and has never been isolated from a naturally occurring source. Although man-made, P4HB homopolymer belongs to a larger class of materials called polyhydroxyalkanoates (PHAs). PHA polymers include naturally occurring polymers produced by wildtype (naturally occurring) microorganisms, and PHA polymers that, like P4HB, are not naturally occurring (Steinbüchel, et al. *FEMS Microbial. Lett.* 128:219-228 (1995) and Agnew, et al., *Chemical Engineering Science*, 103:58-67 (2013)).

Chemical synthesis of P4HB has been attempted, but it has been impossible to produce the polymer with a sufficiently high molecular weight that is necessary for most applications, including melt processing (Hori, et al., *Polymer* 36:4703-4705 (1995); Houk, et al., *J. Org. Chem.*, 73 (7):2674-2678 (2008); and Moore, et al., *Biomaterials*, 26:3771-3782 (2005)). In fact, it has been calculated to be thermodynamically impossible to chemically synthesize a high molecular weight homopolymer under normal conditions (Moore, et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic methods. Poly-4-hydroxybutyrate (P4HB) can be produced, however, using transgenic fermentation methods, see, for example, U.S. Pat. No. 6,548,569 to Williams et al., and is produced commercially, for example, by Tepha, Inc. (Lexington, Mass.). Copolymers of poly-4-hydroxybutyrate can also be produced by transgenic fermentation methods, see also U.S. Pat. No. 6,548,569 to Williams et al.

It should be noted that the literature commonly refers to another polyhydroxyalkanoate, poly-3-hydroxybutyrate (P3HB), simply as polyhydroxybutyrate (PHB) (see Section 2 of Moore, T., et al., *Biomaterials* 26:3771-3782 (2005)). Unlike P4HB, PHB is naturally occurring, and has entirely different properties from P4HB. PHB is structurally and functionally different to P4HB. For example, PHB has a melting temperature of 180° C. versus a melting temperature of about 61° C. for P4HB. The polymers also have substantially different glass transition temperatures and mechanical properties. For example, PHB is a relatively hard brittle polymer with an extension to break of just a few percent, whereas P4HB is a strong extensible polymer with an extension to break of about 1000%. As such, PHB has properties resembling polystyrene whereas P4HB has properties more similar to low density polypropylene. Not surprisingly, substantially different conditions are required to process these two polymers, and the resulting products have substantially different properties.

U.S. Pat. Nos. 6,245,537, 6,623,748, 7,244,442, and 8,231,889 describe methods of making PHA polymers with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III*, 4:91-127 (2002), Martin, et al. *Biochem. Eng. J.* 16:97-105 (2003), and Williams, et al., *Biomed. Tech.* 58(5):439-452 (2013). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering.

(ii) Polymeric Blends

In some embodiments, the P4HB homo- or copolymer is blended with another polymer, preferably a resorbable polymer. Examples of other resorbable polymers include, but are not limited to, polymers containing glycolic acid, lactic acid, 1,4-dioxanone, trimethylene carbonate, 3-hydroxybutyric acid, and ε-caprolactone, and include polyglycolic acid, polyglycolide, polylactic acid, polylactide (including L-, D- and D,L-forms), polydioxanone, polycaprolactone, copolymers of glycolic and lactic acids such as VICRYL® polymer, and the MAXON® and MONOCRYL® polymers. If desired, the P4HB homopolymer and copolymers thereof may also be blended with natural absorbable polymers, such as collagen, silk, proteins, polysaccharides, glycosaminoglycans, hyaluronic acid, heparin, and chitosan, as well as other components prior to preparing the yarns or monofilaments. The ratio of the polymer in the blend to the non-PHA polymer component(s) may be varied in order to select the desired properties of the yarn or monofilament. However, the ratio of the non-PHA to the PHA polymer should not be so high that it causes the resulting yarn to have a tenacity less than 8.1 grams per denier. This also applies to copolymers of P4HB. The ratio of co-monomers in a P4HB copolymer should not be so high that it causes the yarn to have a tenacity less than 8.1 grams per denier.

B. Additives

The P4HB polymer or the polymeric blends can be used in combination with additives, to prepare the high tenacity yarns and monofilaments. The additives may be nucleating agents and/or plasticizers. These additives may be added in sufficient quantity to produce the desired result. Nucleating agents may be incorporated to increase the rate of crystallization of the P4HB homopolymer, copolymer or blend. Such agents may be used to improve the mechanical properties of the yarns and monofilaments, and to reduce cycle times. Additives may generally be added in amounts of up to 20% by weight.

Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl ricinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

Other additives that can be incorporated into the P4HB polymer and copolymers thereof include, but are not limited to, compatibilizers, porogens, dyes, and organic or inorganic powders including fillers and bioceramics. Particularly preferred bioceramics are degradable, and include tricalcium phosphate ($\alpha$ and $\beta$ forms of TCP—with a nominal composition of $Ca_3(PO_4)_2$), biphasic calcium phosphate (BCP), calcium sulfate, calcium carbonate, hydroxyapatite and other calcium phosphate salt-based bioceramics. Bioactive glasses may also be incorporated prior to preparing yarns.

It may also be advantageous to incorporate contrast agents, radiopaque markers, imaging agents, or radioactive substances into the P4HB polymer and copolymers thereof, prior to spinning the high tenacity yarns or monofilaments. Alternatively, these can be incorporated into or onto the high tenacity yarns or monofilaments during subsequent processing steps.

C. Bioactive Agents

Bioactive agents may be incorporated in the compositions disclosed herein. Examples of bioactive agents that can be incorporated into the P4HB polymer, copolymer, or blends thereof, include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, growth factors, fibronectin, laminin, vitronectin, integrins, antibiotics, antimicrobials, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, lipoproteins, hyaluronic acid and derivatives thereof, allograft material, xenograft material, ceramics, nucleic acid molecules, antisense molecules, aptamers, siRNA, nucleic acids, and combinations thereof.

III. Methods of Making

Methods for making yarns with tenacity as high as 8.081 grams per denier with denier per filament ranging tightly from 1.98-2.27 are disclosed in U.S. Pat. No. 8,747,468 to Martin, et al. Yarns produced according to the methods disclosed in U.S. Pat. No. 8,747,468 have about 60% strength retention after implantation for 2 weeks.

P4HB has a melt temperature ranging from 60 to 76° C. (depending upon processing and molecular weight of the polymer). Previous methods used to orient yarns made from P4HB did expose the yarn to heat, but at temperatures less than the melt temperature of P4HB. For example, U.S. Pat. No. 8,747,468 to Martin discloses an orientation roller set at 56° C. to heat the yarn made from a P4HB homopolymer during orientation. This temperature was below the melting temperature of P4HB homopolymer used to make the yarn.

Methods of making monofilament fibers of P4HB are disclosed in U.S. Pat. No. 8,034,270 to Martin, et al., U.S. Pat. No. 7,641,825 to Rizk et al., and U.S. Pat. No. 8,747,468 to Martin, et al. U.S. Pat. No. 8,034,270 to Martin discloses melt extrusion of P4HB fiber, and orientation in a multi-stage process, but does not disclose cold drawing followed by hot drawing at a temperature above the melt temperature of P4HB. U.S. Pat. No. 7,641,825 to Rizk discloses melt extrusion of P4HB fiber, and orientation in a multi-stage process. However, the extrudate was drawn in a heated tube, maintained above the melting temperature of the filament before being quenched in a water bath, drawn through multistage orientation, and then hot stretched (also known as relaxation). Rizk does not disclose a cold draw prior to a hot draw at a temperature above the melt temperature of P4HB. U.S. Pat. No. 8,747,468 to Martin discloses melt extrusion of P4HB monofilament followed by water quenching and conveying into a three-stage orientation, with inline relaxation. Martin does not disclose cold drawing followed by hot drawing at a temperature above the melt temperature of P4HB. U.S. Pat. No. 8,016,883 to Coleman does not describe methods for making monofilament fibers of P4HB, but does disclose a method for making multifilament fibers of P4HB comprising air-quenching P4HB filaments, applying spin finish, and then drawing over a series of godet rolls. Coleman does not disclose cold drawing the P4HB filaments followed by hot drawing the filaments at a temperature above the melt temperature of P4HB. Odermatt et al. *Int. J. Polymer Science*, Article 216137, 12 pages (2012) discloses a monofilament suture made from melt extrusion of P4HB wherein the extruded filaments are quenched, and drawn in line with stretch ratios of 6 to 11× in a multistage drawing process. Odermatt does not disclose a cold draw prior to a hot draw at a temperature above the melt temperature of P4HB. Martin et al., *Biochem. Eng. J.* 16:97-105 (2003) discloses that P4HB can be elongated almost 10 times its original length, but does not disclose the production of P4HB monofilament fibers by cold drawing prior to hot drawing at a temperature above the melt temperature of P4HB.

The methods disclosed herein are based at least on the discovery that yarns made from polymers including the P4HB homopolymer, copolymer or polymeric blends containing P4HB homo- or copolymers, can be oriented to yield tenacities of 8.1 grams per denier or higher if the yarn is exposed to temperatures above its melt temperature during drawing. The methods also improve the production of monofilament fibers of P4HB homopolymer, copolymers or blends thereof if the monofilament fibers are cold drawn and then hot drawn at temperatures above the melt temperature of the P4HB homopolymer, copolymer or blend thereof, and provide more consistent mechanical properties with break strengths preferably greater than 500 MPa, more preferably greater than 800 MPa or 850 MPa, and even more preferably greater than 900 MPa, 1,000 MPa, 1,100 MPa, 1,200 MPa, 1,300 MPa or 1,400 MPa. In contrast to spinning of other thermoplastics such as polypropylene, yarns and monofilaments of P4HB and copolymers thereof should not be drawn immediately after the polymer or copolymer leaves the molten state. U.S. Pat. No. 8,034,270 discloses allowing P4HB extrudate time to crystallize, however, the extrudate was drawn immediately after extrusion, and was allowed dwell time to crystallize, after which further multi stage drawing was possible. By contrast, in the methods disclosed herein, the fiber extrudate is preferably not drawn under tension from the extruder.

The method generally includes the following steps: (i) spin the P4HB homopolymer, copolymer or polymeric blends containing P4HB homopolymer or copolymers thereof into fibers (multifilament or monofilament), (ii) allow the fibers time to crystallize, (iii) cold draw, and (iv) one or more orientation steps of hot drawing. In some embodiments, the last hot drawing orientation step is followed by a relaxation step (also sometimes referred to as "hot stretching"). In each of the hot drawing orientation steps it is essential to keep the yarn or monofilament under tension to prevent the yarn or monofilament from melting (since the methods require hot drawing at a temperature above the melt temperature of the polymer, copolymer or blend). It has been discovered that the P4HB fibers (monofilament or multifilament) can be drawn at temperatures up to 93° C. provided the fibers are kept under tension.

In a preferred embodiment, yarn of P4HB and copolymers thereof with tenacity between 8.1 and 12 grams per denier, more preferably 8.2 and 12 grams per denier and even more preferably 8.5 and 12 grams per denier is obtained by spinning P4HB and copolymers thereof using a multi-hole spinneret, drawing the extruded yarn at a temperature less than 45° C. using an orientation ratio of 2-6, hot drawing the yarn at a temperature above the melt temperature of the polymer or copolymer using an orientation ratio of 0.90-3.0, and more preferably 1.9-3.0, hot drawing the yarn at a temperature above the melt temperature of the polymer or copolymer using an orientation ratio of 0.9-3.0, and or more preferably 1.01-2.5, one or more times, and optionally relaxing the oriented fiber using an orientation ratio between 0.8 and 1.2. In another preferred embodiment, the monofilament of P4HB, copolymer or blend thereof is obtained by spinning P4HB, copolymer or blend thereof, drawing the monofilament at a temperature less than 50° C., more preferably 45° C., using an orientation ratio between 1 and 4, and more preferably between 3 and 4, followed by hot drawing the monofilament at a temperature above the melt temperature of the polymer or copolymer, one or more times, and optionally relaxing the oriented fiber using an orientation ratio between 0.8 and 1.2, more preferably between 1.0 and 1.2. In a particularly preferred embodiment, the monofilament of P4HB, copolymer or blend thereof is obtained by hot drawing the monofilament (after cold drawing) using an orientation ratio between 1.5 and 2.5 in a first hot draw stage, followed by a second hot drawing using an orientation ratio between 1.0 and 1.5, and a third hot drawing using an orientation ratio between 1.0 and 1.5, wherein each of the hot drawings are made at a temperature above the melt temperature of the polymer, copolymer or blend thereof. In an even more preferred embodiment, the spun extrudate of P4HB, copolymer or blend thereof is allowed dwell time to crystallize before it is cold drawn.

A. Spinning of Yarns of P4HB, Copolymers and Blends Thereof

The yarns disclosed herein are produced by fiber spinning. Either solvent spinning or melt spinning may be used to produce the yarns.

In one embodiment, yarns of P4HB, copolymers and blends thereof may be spun as follows: The polymer, copolymer or blend is pelletized, and dried so the moisture content of the polymer, copolymer or blend is less than 300 ppm. The dried pellets are placed in the feed hopper of an extruder, and protected from moisture, for example with a dry nitrogen purge. The pellets are gravity fed into a chilled feeder section, and introduced into a suitable extruder barrel with an extrusion screw. One suitable extruder barrel has a diameter of 0.75 inches and length of 25.69 inches, and is fitted with an extrusion screw with a 30:1 L/D ratio. American Kuhne makes a suitable extruder. In a preferred embodiment, the extruder barrel contains 4 heating zones, and a processing profile is set with temperatures ranging from 40° C. to 300° C. and pressures of 200 psi to 3,000 psi. The heated and softened polymer, copolymer or blend is fed into a metering pump, and from the metering pump the resin is fed into the heated block. The spin head is fitted with a spin pack comprising filtering media (screens), and spinnerets containing the desired number of holes for forming the individual filaments of the yarn. For example, the spinneret may have 15, 30, 60, 120 or more or less holes. The extruded filaments exit the spinneret, and pass through a heated chimney before they are allowed to cool. Spin finish is preferably applied to the yarn, and the yarn may either be collected on a winder, or oriented in-line. Suitable spin finishes include PEG400, Tween 20, PEG40 Stearate, Dacospin and Filapan. In a preferred embodiment, the spin finish is PEG400.

The diameter of the spinneret holes may range from 6 to 10 mil, more preferably their diameter is 8 mil. The exit temperature of the yarn from the spinneret can be between 200 and 240° C., and more preferably, 230° C. The yarn speed is 3-10 m/min, and more preferably 4-6 m/min at the extrudate take up winder.

B. Orientation of Yarns of P4HB, Copolymers and Blends Thereof

According to the methods disclosed herein, yarns of P4HB, copolymers and blends thereof should not be exposed to temperatures above their melt temperatures immediately after spinning and drawn. This results in lower tenacity yarn. High tenacity yarns of P4HB, copolymers and blends thereof can be produced from yarn extrudate if the extrudate is first allowed time to crystallize at ambient temperature, is then "cold" drawn/oriented as disclosed herein, before drawing at a temperature above the melt temperature of the P4HB polymer, copolymer or blend thereof. The drawn yarn may be subsequently drawn further, and if desired, relaxed and/or annealed.

It has been discovered that high tenacity fiber can be produced with slower line speeds. At line speeds of 13 meters/min, multifilament with tenacity of less than 8.1 grams per denier was obtained. Thus, allowing the extrudate more time to crystallize can be accomplished in one embodiment by slowing the line speed. Yarns of P4HB, copolymers, and blends thereof with tenacity greater than 8.1 grams per denier can be made using line speeds of less than 13 meters/min, preferably less than 10 meters/min, and more preferably less than 7 meters/min. In a preferred embodiment, line speed is in a range from 4-6 meters/min.

(i) Cold Drawing/Orientation

The yarn is drawn at a temperature less than 45° C., preferably less than 35° C., and more preferably less than 25° C., using an orientation ratio between 2 and 6. In a preferred embodiment the yarn is drawn at ambient temperature prior to drawing at a temperature above the melt temperature of the polymer or copolymer. In this embodiment, the spun yarn is first drawn at ambient temperature at an orientation ratio between 2 and 6, preferably between 3 and 5, and more preferably, the yarn is drawn at an orientation ratio of 4.

(ii) Hot Drawing/Orientation

The cold drawn-yarn is hot drawn in a second orientation step at a temperature above the melt temperature of the polymer or copolymer. Preferably the cold drawn yarn is exposed to a temperature between 62° C. and 100° C., more preferably 67° C. to 95° C., and even more preferably from 75° C. to 85° C. In a particularly preferred embodiment, the yarn is exposed to a temperature between 67° C. to 95° C., and the yarn is drawn with an orientation ratio between 1.9 and 3.0.

In some embodiments, the yarn is heated by exposure to heated orientation rollers. The orientation rollers are set at temperatures between 62° C. and 100° C., more preferably 67° C. and 95° C., and the yarn is drawn using an orientation ratio between 0.90 and 3.0, and more preferably between 1.9 and 3.0. In other embodiments, the yarn may be heated by exposure to a heat source between the orientation rollers. For example, the yarn may be heated by passage through a hot liquid bath, for example a hot water bath, and then drawn at an orientation ratio of 0.90 and 3.0, and more preferably between 1.9 and 3.0.

After cold drawing and hot drawing the yarn, the yarn may subsequently be drawn in one or more additional orientation steps, preferably at a temperature above the polymer, copolymer or blend's melt temperature. In a preferred embodiment, the yarn is drawn one or two more times at a temperature above the melt temperature of the polymer, copolymer or blend using an orientation ratio between 0.90 and 3.0, and more preferably 1.01 and 2.5. These steps may be performed, for example, by setting the temperatures of the orientation rollers for the third and optionally fourth orientation steps to temperatures between 62° C. and 100° C.

In one preferred embodiment, the yarn is oriented using a 3 to 6-step orientation process, and more preferably a 3 to 4-step process. In the first orientation step, the yarn is oriented at a temperature above −10° C. In a preferred embodiment, ambient temperature determines the first temperature which could be anything up to 45° C., but more likely around 20-25° C. Preferably however, in the first orientation step, the yarn is oriented at a temperature less than 45° C., more preferably less than 35° C. and even more preferably less than 25° C., using an orientation ratio between 2 and 6. In the second orientation step, the yarn is oriented at a temperature between 62° C. and 100° C., more preferably between 67° C. and 95° C., and even more preferably between 75° C. and 85° C. using an orientation ratio of 1.9 to 3.0. In the third orientation step, the yarn is oriented at a temperature between 62° C. and 100° C., more preferably between 67° C. and 95° C., and even more preferably between 75° C. and 85° C. using an orientation ratio of 0.90-3.0, and more preferably 1.01 to 2.5. Optionally, a fourth orientation step may be added wherein the yarn is oriented at a temperature between 62° C. and 100° C., more preferably between 67° C. and 95° C., and even more preferably between 75° C. and 85° C. using an orientation ratio of 0.90-3.0, and more preferably 1.01 to 2.5. The method includes optional additional orientation steps, using an appropriate orientation ratio.

In each of the hot orientation steps it is essential to keep the yarn under tension to prevent the yarn from melting.

(iii) Relaxation

In some embodiments, the drawn yarn may be relaxed. For example, the yarn may be relaxed after the final hot draw. In a preferred embodiment, the yarn is relaxed using an orientation ratio between 0.7 and 1.0 at a temperature less than 45° C., more preferably less than 35° C., and even more preferably less than 25° C. For example, the yarn may be relaxed in a step where the godets are set at a temperature less than 45° C., more preferably less than 35° C., and even more preferably less than 25° C. or at ambient temperature. In another preferred embodiment the yarn may be relaxed using a first heated godet. The first godet could be heated for example to a temperature of about 60±40° C. and a second unheated godet using an orientation ratio between 0.8 and 1.2. In this configuration, the yarn is heated by the first godet, but not by the second godet.

C. Spinning of Monofilaments of P4HB, Copolymers and Blends Thereof

The monofilaments disclosed herein are produced by fiber spinning. Either solvent spinning or melt spinning may be used to produce the monofilaments.

In one embodiment, monofilament fibers of P4HB, copolymers, and blends thereof may be spun as follows: The polymer, copolymer or blend is pelletized, and dried so the moisture content of the polymer, copolymer, or blend is less than 300 ppm. The dried pellets are placed in the feed hopper of an extruder, and protected from moisture, for example with a dry nitrogen purge. The pellets are gravity fed into a chilled feeder section, and introduced into a suitable extruder barrel with an extrusion screw. One suitable extruder barrel has a diameter of 0.75 inches and length of 25.69 inches, and is fitted with an extrusion screw with a 30:1 L/D ratio. American Kuhne makes a suitable extruder. In a preferred embodiment, the extruder barrel contains 4 heating zones, and a processing profile is set with temperatures ranging from 40° C. to 300° C. and pressures of 200 psi to 3,000 psi. The heated and softened polymer, copolymer or blend is fed into a metering pump, and from the metering pump the resin is fed into the heated block. The spin head is fitted with a spin pack comprising filtering media (screens), and spinnerets containing the desired number of holes for forming the individual monofilaments. For example, the spinneret may have 1, 4, 8, 16 or more or less holes. The extruded monofilaments exit the spinneret, and are allowed to cool. The exit temperature of the monofilament from the spinneret is preferably between 200 and 240° C., and more preferably, 230° C. In an embodiment, the monofilaments are quenched after extrusion, preferably by extrusion directly into a water bath. In a preferred embodiment the water temperature is set between 5° C. and ambient, and more preferably at about 16° C.±6° C.

In an embodiment, the extruded monofilament is allowed additional time to crystallize prior to orientation. The additional time required for crystallization depends on the diameter of the fiber, and can range from 30 seconds to 20 minutes, more preferably 1 minute to 15 minutes, and even more preferably 4 minutes to 12 minutes. Longer times are required for larger diameter fibers. For example, a monofilament size 5/0 suture should preferably be allowed to crystallize for 3-5 minutes prior to orientation, whereas a monofilament size 1 should be allowed preferably 10-15 minutes to crystallize before orientation. In a preferred embodiment, the monofilament is quenched in a water bath, and then allowed additional time to crystallize prior to orientation.

D. Orientation of Monofilaments of P4HB and Copolymers Thereof

According to the methods disclosed herein, monofilaments of P4HB and copolymers thereof should not be exposed to temperatures above their melt temperatures immediately after spinning, and they should not be immediately drawn. This results in lower tensile strength fiber. High strength monofilaments of P4HB and copolymers thereof can be produced from monofilament extrudate if the extrudate is first allowed time to crystallize at ambient temperature (or a temperature less than 50° C., more preferably less than 45° C.), is then "cold" drawn/oriented as disclosed herein, before drawing at a temperature above the melt temperature of the P4HB polymer or copolymer. The drawn monofilament may be subsequently drawn further, and if desired, relaxed and/or annealed.

(i) Cold Drawing/Orientation

The monofilament fiber is drawn at a temperature less than 50° C., preferably less than 45° C. or 35° C., and more preferably less than 30° C., using an orientation ratio between 1 and 4. In a preferred embodiment the monofilament fiber is drawn at ambient temperature prior to drawing at a temperature above the melt temperature of the polymer or copolymer. In this embodiment, the spun monofilament is first drawn at ambient temperature at an orientation ratio between 1 and 4, preferably between 2 and 4, and more preferably, the monofilament is drawn at an orientation ratio between 3 and 4 or 3.5±0.5.

(ii) Hot Drawing/Orientation

The cold drawn monofilament is hot drawn in a second orientation step at a temperature above the melt temperature of the polymer, copolymer or blend. Preferably the cold drawn monofilament is exposed to a temperature between 62° C. and 100° C., more preferably 70° C. to 98° C., and even more preferably from 85° C. to 95° C. In a particularly preferred embodiment, the monofilament is exposed to a temperature between 85° C. to 95° C., and the monofilament is drawn with an orientation ratio between 1.5 and 2.5 after the cold draw. To avoid melting of the fiber, it is essential that the monofilament remain under tension when it is exposed to temperatures above 50° C., more preferably above its melt temperature, during orientation.

In some embodiments, the monofilament is heated by exposure to heated orientation rollers. The orientation rollers are set at temperatures between 62° C. and 100° C., more preferably 67° C. and 95° C., and the monofilament is drawn using an orientation ratio between 1.5 and 2.5, and more preferably between 1.7 and 2.3. In other embodiments, the monofilament may be heated by exposure to a heat source between the orientation rollers. For example, the monofilament may be heated by passage through a hot liquid bath, for example a hot water bath, and then drawn at an orientation ratio between 1.5 and 2.5, and more preferably between 1.7 and 2.3.

After cold drawing and hot drawing the monofilament, the monofilament may subsequently be drawn in one or more additional orientation steps, preferably at a temperature above the polymer, copolymer or blend's melt temperature. In a preferred embodiment, the monofilament is drawn one or two more times at a temperature above the melt temperature of the polymer, copolymer or blend using an orientation ratio between 1.0 and 1.5, and more preferably 1.01 and 1.2. These steps may be performed, for example, by passing the monofilament through a hot liquid bath, for example a hot water bath, set at a temperature preferably between 62° C. and 100° C., and more preferably between 85° C. and 95° C.

In one preferred embodiment, the monofilament is oriented using a 3 to 6-step orientation process, and more preferably a 3 to 4-step process. In the first orientation step, the monofilament is oriented at a temperature above −10° C. In a preferred embodiment, ambient temperature determines the first temperature which could be anything up to 45° C., but more likely around 14-30° C. Preferably however, in the first orientation step, the monofilament is oriented at a temperature less than 45° C., more preferably less than 35° C. and even more preferably less than 25° C., using an orientation ratio between 1 and 4. In the second orientation step, the monofilament is oriented at a temperature between 62° C. and 100° C., more preferably between 67° C. and 95° C., and even more preferably between 75° C. and 95° C. using an orientation ratio of 1.5 to 2.5. In the third orientation step, the monofilament is oriented at a temperature between 62° C. and 100° C., more preferably between 67° C. and 95° C., and even more preferably between 75° C. and 95° C. using an orientation ratio of 1.0-1.5, and more preferably 1.01 to 1.2. Optionally, a fourth orientation step may be added wherein the monofilament is oriented at a temperature between 62° C. and 100° C., more preferably between 67° C. and 95° C., and even more preferably between 75° C. and 95° C. using an orientation ratio of 1.0-1.5, and more preferably 1.01 to 1.2. The method includes optional additional orientation steps, using an appropriate orientation ratio.

In each of the hot orientation steps it is essential to keep the monofilament under tension to prevent the monofilament from melting.

Table 2 shows the effect of increasing the temperature of the first orientation step during the production of a P4HB monofilament with a diameter of 0.171±0.002 mm (size 5/0 suture fiber), elongation of 28.7±1.4%, and with the water bath temperature of the second orientation step held constant at 93° C. As shown in Table 2, cold drawing the monofilament at ambient temperature (approx. 21-25° C.) with an orientation ratio of 3.5, and then hot drawing above the melt temperature of P4HB (at a temperature of 93° C.) yielded an oriented monofilament fiber with an overall draw ratio of 6.7, and tensile strength of 898 MPa. Attempting to increase the draw ratio in the first orientation step over 4.0 increased fiber tension and resulted in the necking line retreating on the first roller. This caused flattening of the fiber extrudate due to compression against the surface of the roller under very high tension. The monofilament should therefore preferably not be oriented with a draw ratio of more than 4.0 during cold drawing. Increasing the temperature of the first orientation step to 50° C. decreased tension on the monofilament during drawing, but caused the necking line of the extrudate to advance from the top of the roller into the water bath (positioned between the rollers) and soften. Advancement of the extrudate could be prevented by increasing the draw ratio from 3.5 to 4.0, however subsequent drawing had to be decreased to prevent breakage of the monofilament. As a result, increasing the temperature of the first orientation step to 50° C. resulted in the same overall orientation of 6.7, but yielded a monofilament with a lower tensile strength (see second entry of Table 2 compared to first entry). When the temperature of the water bath between the first stage rollers was increased to 70° C. or 90° C., the initial draw ratio had to be increased to 4.6 and 5.08, respectively, in order to prevent the necking line of the extrudate from advancing into the water bath and breaking (due to softening and melting). However, increasing the temperature of the first orientation step so that it was higher than the melt temperature of the P4HB monofilament resulted in a significant drop in the tensile strength of the monofilaments even though the overall draw ratio remained the same (6.7). When the initial orientation step was performed at 70° C., the tensile strength of the fiber decreased to 707 MPa compared to 898 MPa for the fiber initially cold drawn at ambient temperature. The tensile strength of the fiber decreased further to 657 MPa when the temperature of the initial orientation step was increased to 90° C. These examples thus demonstrate (i) the improved tensile strength properties of monofilaments that can be obtained by using a cold draw followed by a hot draw at a temperature above the melt temperature of the monofilament, (ii) the ability to hot draw the monofilament at temperatures well in excess of the monofilament's melt temperature, and (iii) the difficulties of orienting a very soft monofilament fiber with a low softening temperature, wherein the monofilament can be readily deformed if the applied tension is too high. Importantly, the results of Table 2 and additional examples described herein demonstrate that an initial cold draw followed by hot drawing at a temperature above the melt temperature of the polymer can be used to produce monofilaments of P4HB, copolymers and blends thereof with tensile strengths much higher than previously reported with tensile strength reaching up to 1,200 MPa, 1,300 MPa or 1,400 MPa.

TABLE 2

Effect of Increasing Temperature on Initial Draw of P4HB Monofilament Extrudate

| First Orientation | | Second | Overall | Tensile | |
| --- | --- | --- | --- | --- | --- |
| Temperature (° C.) | Draw Ratio | Orientation Draw Ratio | Draw Ratio | Load (kgf) | Stress (MPa) |
| Ambient | 3.50 | 1.87 | 6.7 | 2.16 | 898 |
| 50 | 4.00 | 1.65 | 6.7 | 2.04 | 874 |
| 70 | 4.60 | 1.42 | 6.7 | 1.61 | 707 |
| 90 | 5.08 | 1.25 | 6.7 | 1.55 | 657 |

Table 3 shows examples of the tensile properties of P4HB monofilament fibers that can be produced by the methods described herein. Examples are provided for USP suture sizes ranging from 8-0 to 1. Or, suture diameters ranging from 0.063 mm to 0.510 mm. Notably, the tensile strengths of the P4HB monofilament sutures are in the range of 1,000 to 1,300 MPa.

TABLE 3

Tensile Properties of P4HB Monofilaments Produced by Cold Drawing followed by Hot Drawing

| Monofilament Size | Total Draw Ratio | Diameter (mm) | Elongation to Break (%) | Tensile Strength (MPa) |
| --- | --- | --- | --- | --- |
| 8-0 | 5.50 | 0.063 | 17.5 | 1,124 |
| 6-0 | 7.06 | 0.119 | 26.5 | 1,198 |
| 5-0 | 7.38 | 0.155 | 22.0 | 1,282 |
| 3-0 | 7.84 | 0.294 | 28.5 | 1,057 |
| 0 | 8.49 | 0.452 | 30.9 | 1,031 |
| 1 | 8.88 | 0.510 | 33.1 | 1,090 |

(iii) Relaxation

In some embodiments, the monofilament may be relaxed. For example, the monofilament may be relaxed after the final hot draw. In a preferred embodiment, the monofilament is relaxed using an orientation ratio between 0.6 and 1.0, more preferably 0.6 and 0.9, and at a temperature less than 74° C. For example, the monofilament may be relaxed in a step where the monofilament passes through a hot liquid bath, such as a hot water bath, set at a temperature less than 74° C. In another preferred embodiment the monofilament may be relaxed using a first heated godet. The first godet could be heated for example to a temperature of about 60±40° C. and a second unheated godet using an orientation ratio between 0.6 and 1.0. In this configuration, the monofilament is heated by the first godet, but not by the second godet.

E. Addition of Bioactive Agents/Additives

Bioactive agents may be incorporated in the compositions disclosed herein either prior to spinning the yarns, for example, during blending or pelletization, or alternatively, these agents may be incorporated into or onto the yarns or products made from the yarns during subsequent processing steps.

The bioactive agents, and the P4HB homopolymer or copolymer, may be dissolved in a solvent or solvent system in order to disperse the bioactive agent in the P4HB homopolymer or copolymer, and the solvent may then be removed by evaporation. Preferred solvents include methylene chloride, chloroform, tetrahydrofuran, acetone, dimethylformamide, and 1,4-dioxane.

Alternatively, the bioactive agents may be dissolved to form a solution or suspended in a solution, and applied to the oriented yarn. Solutions and suspensions may be applied to the yarn by spray coating, dip-coating, immersion, painting, electrostatic spraying, pad printing, wiping, and brushing. In a preferred embodiment, the bioactive agents are dissolved in non-solvents for P4HB and copolymers thereof so that the bioactive agents may be applied to the yarn without causing any significant loss of tenacity. After application of the bioactive agents, non-volatile solvents, such as water, may be removed by vacuum drying. This is particularly important to protect the yarn from hydrolysis, and loss of polymer molecular weight. Solvents that may be used to coat the yarns with bioactive agents include, but are not limited to, water, alcohols including methanol, ethanol and isopropanol, ether, hexane and other non-polar organic solvents.

Where additives are employed, the additives may also be added to the polymers and copolymers prior to preparing the high tenacity yarns. Preferably, additives are incorporated during the compounding process to produce pellets that can be subsequently processed into yarns. Additives may also be incorporated using a solution-based process. The additives are preferably biocompatible, and even more preferably the additives are both biocompatible and resorbable.

In one embodiment, the additives are nucleating agents and/or plasticizers. These additives may be added in sufficient quantity to produce the desired result. In general, additives if included, are added in amounts of up to 20% by weight.

IV. Methods of Manufacturing Devices from High Tenacity Yarns and High Tensile Strength Monofilaments of P4HB and Copolymers Thereof The multifilament yarns and monofilament fibers disclosed herein have prolonged strength in vivo making them suitable for soft tissue repairs where high strength is required and also needs to be maintained for a prolonged period. Other examples of applications for the high strength yarn and monofilament fibers include soft and hard tissue repair, replacement, remodeling, and regeneration include wound closure, breast reconstruction and breast lift, including mastopexy procedures, lift procedures performed on the face such as face-lifts, neck lifts, and brow lifts, ligament and other tendon repair procedures, abdominal closure, hernia repairs, anastomosis, and pelvic floor reconstruction.

A. Sutures and Braids

The yarns may be used to prepare high strength multifilament sutures, hybrid sutures of monofilament and multifilament fibers that have excellent pliability, high knot strength, good drape, and can be securely knotted forming soft knot bundles with a low profile. For example, the yarns may be processed into resorbable high strength sutures and suture anchors that can be used in rotator cuff repair procedures. Currently, these procedures are repaired with permanent sutures because existing resorbable sutures degrade too quickly. In contrast to existing resorbable sutures, sutures prepared with the high tenacity yarn of the present invention not only provide high initial strength to stabilize a repair under a significant load, but also lose strength slowly allowing the repair of the soft tissues. The high strength sutures may also be used in bone anchors, suture anchors, and soft suture anchors. These sutures and anchors are particularly useful for shoulder, elbow, wrist, hand hip, knee, ankle, and foot repairs, including tendon and ligament repairs, as well as in lift and suspension procedures. The bone anchors, suture anchors and soft suture anchors may incorporate one or more needles, yarns of different colors, and if desired, flat braided sections. The ability to use resorbable high tenacity sutures, suture anchors, bone anchors, and soft suture anchors for procedures such as rotator cuff repair eliminates longer-term complications that can arise from foreign bodies, such as permanent sutures. These sutures may be used, for example, in soft tissue approximation, anastomosis, suspension and lift procedures, and for other applications in plastic surgery.

In another embodiment, the yarns may be used to prepare flat suture tapes, including flat braided suture tapes. These suture tapes are useful in approximation and/or ligation of soft tissue, and are particularly useful in procedures requiring broad compression and increased cut-through resistance. For example, the suture tapes can be used in shoulder and rotator cuff repair procedures such as acromioclavicular repairs, and restoration of labral height in instability repairs, as well as in ACL and PCL repair procedures. The suture tapes may have flat ends, tapered ends, needles at one or both ends of the suture tape, and comprise yarns with one or more different dyes.

Suture braids may be produced from the yarns with US Pharmacopeia (USP) suture sizes of 12-0, 11-0, 10-0, 9-0, 8-0, 7-0, 6-0, 5-0, 4-0, 3-0, 2-0, 0, 1, 2, 3, 4, and 5, and meet the knot-pull tensile strengths for these sizes. In another embodiment, the suture braids may be oversized in diameter in order to meet USP knot-pull tensile strengths. For example, the diameter of the suture braids maybe oversized by up to 0.3 mm, preferably 0.2 mm, more preferably 0.1, and even more preferably 0.05 mm. The sutures may be needled and/or contain loops at either end.

The sutures disclosed herein and any devices in need thereof for example, circular knits, may also be coated to improve lubricity. Coatings that can be applied to increase the lubricity of the braided sutures include wax, natural and synthetic polymers such as polyvinyl alcohol, and spin finishes including Tween® 20, and polymers or oligomers of ethylene oxide, propylene oxide, PEG400, PEG40 Stearate, Dacospin and Filapan. These coatings are preferably applied so the braided suture has a coating weight of less than 6 wt %, more preferably less than 3 wt %, and even more preferably less than 2 wt %. It is preferred that the coatings readily leave the surface of the braided suture in vivo, for example, by degradation or dissolution (for example if the coating is water-soluble.)

In another embodiment, a coating may be applied to the surface of the suture in order to slow degradation and increase strength retention in vivo. For example, the suture may be coated with another polymer, preferably a slowly degrading polymer or composition, or coated with wax. For example, the suture may be coated with polycaprolactone to slow degradation, and prolong strength retention.

Braids (including suture tapes and suture braids) made from high tenacity yarns of P4HB and copolymers thereof are preferably prepared by coating the yarn with spin finish, twisting or plying the yarn, and winding onto bobbins. A preferred spin finish is PEG400. The bobbins are then placed on a braider. The number of picks per inch may be increased to improve the fineness of the braid, as desired. The number of picks per inch can range from 5 to 100, and preferably 30 to 60. In some embodiments, cores of monofilament, yarn, or multiple plied yarn strands may be incorporated into the center of the braid. Alternatively, the braids may be prepared without cores.

Examples of the properties of two types of high strength P4HB braids, made with a 16-carrier braider, are shown in Table 4. The braids are made of 30-filament yarn, 5-denier per filament, with a tenacity of 9.4 grams per denier. The braids are constructed of a 16 carriers sheath and 4 to 5 plied cores. The high strength P4HB braids notably have substantially higher tensile strengths (breaking load) than size 2 VICRYL® suture as shown in Table 4. The braids also have a substantially lower Young's Modulus than the VICRYL® suture.

TABLE 4

Properties of Braids Made from High Tenacity P4HB Yarn

| Construction | Diameter (mm) | Breaking Load (kgf) | Stress (kgf/mm$^2$) | Break Elongation (%) | Young's Modulus (GPa) |
|---|---|---|---|---|---|
| P4HB: 16 carrier x 4 bundles | 0.632 | 25.1 | 80.0 | 36.5 | 0.95 |
| P4HB: 16 carrier x 5 bundles | 0.663 | 26.2 | 76.0 | 36.4 | 0.92 |
| VICRYL®: Size 2 | 0.6 | 17.8 | 64.7 | 23.8 | 2.7 |

Examples of the properties of high strength P4HB suture tapes, made with 30-filament yarn of 2.2 denier per filament, with tenacity of 8.2 grams per denier, are shown in Table 5. The properties may be further selected using yarns with different numbers of filaments, deniers per filaments, tenacities, and constructions.

The monofilament fibers may also be used to prepare high strength monofilament sutures, hybrid sutures of monofilament and multifilament fibers that have excellent pliability, high knot strength, and can be securely knotted with low profile knot bundles (i.e. secured with fewer throws than is typical for commercial resorbable monofilament sutures). In one embodiment the monofilament fibers may be processed into resorbable high strength sutures and suture anchors that can be used, for example, in rotator cuff repair procedures. These sutures and anchors are particularly useful for shoulder, elbow, wrist, hand hip, knee, ankle, and foot repairs, including tendon and ligament repairs, as well as in soft tissue approximation, ligation of soft tissue, abdominal closure, and plastic surgery procedures such as lift and suspension procedures, including face and breast lift procedures and breast reconstruction. The monofilament sutures and suture anchors (including soft suture anchors) may incorporate one or more needles, be transparent or dyed, and if desired, braided as part of a suture or suture anchor, or braided into flat tapes.

TABLE 5

Properties of Suture Tapes Made from High Tenacity P4HB Yarn

| Tape Width (mm) | Thickness (mm) | Breaking Load (kgf) | Break Elongation (%) | Young's Modulus (GPa) |
|---|---|---|---|---|
| 2.26 | 0.357 | 40.0 | 30.9 | 5.77 |
| 3.09 | 0.486 | 63.2 | 33.9 | 3.27 |
| 3.74 | 0.51 | 85.2 | 38.4 | 3.54 |

B. Mesh Products

Mesh products may be produced from the high tenacity yarns and high tensile strength monofilaments of P4HB, copolymers, and blends thereof, for example, by warp or weft knitting processes. The mesh can be combined with a P4HB film on one side to make an implant. Non-woven meshes may be prepared from the high tenacity yarns by entangling fibers using mechanical methods. The properties of the nonwovens can be tailored by selection of parameters such as fiber diameter, fiber orientation, and length of the fibers (for staple nonwovens). In a preferred embodiment, the non-woven meshes prepared from the high tenacity yarns have one or more of the following properties (i) a thickness of 0.1-5 mm, (ii) an areal density of 5 to 800 g/m$^2$, (iii) a suture pullout strength of greater than 10 N, and (iv) a burst strength that is able to withstand a pressure of at least 0.1 kPa.

In a further embodiment of the invention, the high tenacity yarns of P4HB and copolymers thereof, may be knit to produce circular knits. Circular knits comprising the high tenacity yarns may be used, for example, as vascular grafts. In one embodiment, a circular knit of the high tenacity yarns of P4HB and copolymers thereof may be produced using a single feed, circular weft knitting machine (Lamb Knitting Co., model ST3A/ZA).

The sutures, braids, suture tapes, meshes, patches and circular knits made from the high tenacity yarns of P4HB and copolymers thereof may be used in ligament and tendon repairs, Bankart lesion repair, SLAP lesion repair, acromionclavicular repair, capsular shift/capsulolabral reconstruction, deltoid repair, Labral repair of the shoulder, Capsular/Labral Repairs of the Hip, rotator cuff tear repair, biceps tenodesis, foot and ankle medial/lateral repair and reconstruction, mid- and forefoot repair, Hallux valgus reconstruction, metatarsal ligament/tendon repair and reconstruction, Achilles tendon repair, ulnar or radial collateral ligament reconstruction, lateral epicondylitis repair, biceps tendon reattachment, knee extra-capsular repair, iliotibial band tenodesis, patellar tendon repair, vastus medialis obliquus (VMO) advancement, knee joint capsule closure, hand and wrist collateral ligament repair, scapholunate ligament reconstruction, tendon transfers in phalanx, volar plate reconstruction, acetabular labral repair, anterior ligament repair, spinal repair, fracture fixation, cardiovascular surgery, general surgery, gastric surgery, bowel surgery, abdominoplasty, plastic, cosmetic and reconstructive surgery including lift procedures, forehead lifting, brow lifting, eyelid lifting, facelift, neck lift, breast lift, lateral canthopexy, elevation of the nipple, breast reconstruction, breast reduction, breast augmentation, mastopexy, pelvic floor reconstruction, cystocele and rectocele repair, low anterior resection, urethral suspension, obstetrics and gynecological surgery, Nissen Fundoplication, myomectomy, hysterectomy, sacrolpopexy, cesarean delivery, hernia repair, general soft tissue approximation and ligation, wound closure including closure of deep wounds and the reduction of wide scars and wound hernias, hemostasis, anastomosis, abdominal closure, laparoscopic procedures, partial nephrectomy, vascular grafting, and implantation of cardiac rhythm management (CRM) devices, including pacemakers, defibrillators, generators, neurostimulators, ventricular access devices, infusion pumps, devices for delivery of medication and hydration solutions, intrathecal delivery systems, pain pumps, and other devices to provide drugs or electrical stimulation to a body part.

In a particularly preferred embodiment, the high strength monofilament fibers can be knitted or woven to make mesh products. In one embodiment, monofilament knitted mesh can be prepared using the following procedure. Forty-nine (49) spools of high strength P4HB monofilament mesh is mounted on a creel, aligned side by side and pulled under uniform tension to the upper surface of a "kiss" roller. The "kiss" roller is spinning while semi-immersed in a bath filled with a 10% solution of Tween® 20 lubricant. The Tween® 20 lubricant is deposited on the surface of the sheet of fiber. Following the application of Tween® 20, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll ready for scoring. The P4HB monofilament mesh is then scored ultrasonically with water, and may be (i) heat set in hot water, and then (ii) washed with a 70% aqueous ethanol solution.

In an embodiment, the meshes made from P4HB monofilaments have one or more of the following properties: (i) a suture pullout strength of at least 1 Kgf, (ii) a burst strength of 0.1 to 100 Kg, (iii) a thickness of 0.05-5 mm, (iv) an areal density of 5 to 800 g/m$^2$, and (v) pore diameter of 5 µm to 5 mm. In a preferred embodiment, the monofilament meshes have one or more of the following properties: (i) a suture pullout strength of 1 Kgf to 20 Kgf, (ii) a burst strength of 1 to 50 Kg, more preferably 10 to 50 Kg, (iii) a thickness of 0.1 to 1 mm, (iv) areal density of 100 to 300 g/m$^2$, and (v) pore diameter 100 µm to 1 mm. In another preferred embodiment, the P4HB monofilament mesh has substantially one or more of the following properties: a pore diameter of 500±100 µm, thickness of 0.5±0.2 mm, areal density of approx. 182±50 g/m$^2$, suture pullout strength of 5.6±2 kgf, and a burst strength of at least 15 Kg, and more preferably at least 24.5 Kg.

In another embodiment, the P4HB meshes may comprise different sized fibers or other non-P4HB fibers, including multifilament, and fibers made from other absorbable or non-absorbable biocompatible polymers and hybrid meshes.

Devices made from the high tenacity yarns and monofilament fibers of P4HB and copolymers thereof may be sterilized using ethylene oxide gas, and even more preferably using an ethylene oxide cold cycle. In another preferred embodiment, the devices may be sterilized with electron-beam irradiation or gamma-irradiation. In another embodiment, the devices may be sterilized using alcohol. The sterility of the devices may be maintained by packaging of the devices in packages designed to protect the devices from contamination and maintain sterility.

C. Other Devices and Indications

The yarns and monofilament fibers may be used to prepare knitted and woven meshes, non-woven meshes, suture tapes, and patches. These mesh and patch products are particularly useful for soft tissue repair, hernia repair, breast lifts, breast reconstructions, face and neck lifts, pelvic floor reconstruction, organ salvage, lift and suspension procedures, and for making enclosures, pouches, holders, covers, clamshells, and casings to hold implantable medical devices.

In view of their mechanical properties, the yarns and monofilament fibers disclosed herein may also be used to prepare medical devices including sutures, braided sutures, hybrid sutures of monofilament and multifilament fibers, suture tapes, braids, ligatures, tapes, knitted or woven meshes, knitted tubes, multifilament meshes, patches, wound healing devices, bandages, wound dressings, burn dressings, ulcer dressings, skin substitutes, hemostats, tracheal reconstruction devices, organ salvage devices, dural substitutes, dural patches, nerve regeneration or repair devices, hernia repair devices, hernia meshes, hernia plugs, device for temporary wound or tissue support, tissue engineering scaffolds, guided tissue repair/regeneration devices, anti-adhesion membranes, adhesion barriers, tissue separation membranes, retention membranes, slings, devices for pelvic floor reconstruction, urethral suspension devices, devices for treatment of urinary incontinence, devices for treatment of vesicoureteral reflux, bladder repair devices, sphincter muscle repair devices, suture anchors, soft suture anchors, bone anchors, ligament repair devices, ligament augmentation devices, ligament grafts, anterior cruciate ligament repair devices, tendon repair devices, tendon grafts, tendon augmentation devices, rotator cuff repair devices, meniscus repair devices, meniscus regeneration devices, articular cartilage repair devices, osteochondral repair devices, spinal fusion devices, stents, including coronary, cardiovascular, peripheral, ureteric, urethral, urology, gastroenterology, nasal, ocular, or neurology stents, stent grafts, cardiovascular patches, vascular closure devices, intracardiac septal defect repair devices, including but not limited to atrial septal defect repair devices and PFO (patent foramen ovale) closure devices, left atrial appendage (LAA) closure devices, pericardial patches, vein valves, heart valves, vascular grafts, myocardial regeneration devices, periodontal meshes, guided tissue regeneration membranes for periodontal tissue, embolization devices, anastomosis devices, cell seeded devices, controlled release devices, drug delivery devices, plastic surgery devices, breast lift devices, mastopexy devices, breast reconstruction devices, breast augmentation devices (including devices for use with breast implants), breast reduction devices (including devices for removal, reshaping and reorienting breast tissue), devices for breast reconstruction following mastectomy with or without breast implants, facial reconstructive devices, forehead lift devices, brow lift devices, eyelid lift devices, face lift devices, rhytidectomy devices, thread lift devices (to lift and support sagging areas of the face, brow and neck), rhinoplasty devices, device for malar augmentations, otoplasty devices, neck lift devices, mentoplasty devices, cosmetic repair devices, devices for facial scar revision, and enclosures, pouches, holders, covers, clamshells, casings to hold implantable medical devices.

The sutures, braids, suture tapes, meshes, patches and circular knits made from the high tenacity yarns and monofilament fibers of P4HB and copolymers thereof may be used in ligament and tendon repairs, hernia repairs, pelvic floor reconstruction, Bankart lesion repair, SLAP lesion repair, acromion-clavicular repair, capsular shift/capsulolabral reconstruction, deltoid repair, Labral repair of the shoulder, Capsular/Labral Repairs of the Hip, rotator cuff tear repair, biceps tenodesis, foot and ankle medial/lateral repair and reconstruction, mid- and forefoot repair, Hallux valgus reconstruction, metatarsal ligament/tendon repair and reconstruction, Achilles tendon repair, ulnar or radial collateral ligament reconstruction, lateral epicondylitis repair, biceps tendon reattachment, knee extra-capsular repair, iliotibial band tenodesis, patellar tendon repair, VMO advancement, knee joint capsule closure, hand and wrist collateral ligament repair, scapholunate ligament reconstruction, tendon transfers in phalanx, volar plate reconstruction, acetabular labral repair, anterior ligament repair, spinal repair, fracture fixation, cardiovascular surgery, general surgery, gastric surgery, bowel surgery, abdominoplasty, plastic, cosmetic and reconstructive surgery including lift procedures, forehead lifting, brow lifting, eyelid lifting, facelift, neck lift, breast lift, lateral canthopexy, elevation of the nipple, breast reconstruction, breast reduction, breast augmentation, mastopexy, cystocele and rectocele repair, low anterior resection, urethral suspension, obstetrics and gynecological surgery, Nissen Fundoplication, myomectomy, hysterectomy, sacrolpopexy, cesarean delivery, general soft tissue approximation and ligation, wound closure including closure of deep wounds and the reduction of wide scars and wound hernias, hemostasis, anastomosis, abdominal closure, laparoscopic procedures, partial nephrectomy, vascular grafting, and implantation of cardiac rhythm management (CRM) devices, including pacemakers, defibrillators, generators, neurostimulators, ventricular access devices, infusion pumps, devices for delivery of medication and hydration solutions, intrathecal delivery systems, pain pumps, and other devices to provide drugs or electrical stimulation to a body part V. Methods of Implanting Devices Made from High Tenacity Yarns and High Tensile Strength Monofilaments of P4HB and Copolymers Thereof The devices made from high tenacity yarns of P4HB and copolymers thereof may be implanted using conventional open surgical techniques, but may also be implanted using minimally invasive techniques. In one embodiment, high strength sutures are implanted using arthroscopic techniques. In a particularly preferred embodiment, the high strength sutures and suture tapes are used for arthroscopic repair of shoulders, elbows, wrists, spine, hips, knees, ankles and feet, including ligament and tendon repair. In another embodiment, meshes made from the high tenacity yarns of P4HB and copolymers thereof may be implanted using laparoscopic techniques. In a particularly preferred embodiment, meshes are implanted for the repair of hernias, and lift procedures, such as mastopexy, using laparoscopic techniques and other minimally invasive techniques.

The present invention will be further understood by reference to the following non-limiting examples.

EXAMPLES

Example 1

Production of 60-Filament P4HB Yarns

Bulk P4HB resin in pellet form with molecular weight of 200-500 KDa was dried to less than 300 ppm water using a rotary vane vacuum pump system. The dried resin was transferred to an extruder feed hopper with nitrogen purge to keep the pellets dry. The extruder used had a ¾" diameter barrel and an extrusion screw with a 30:1 L/D ratio. The extrusion barrel contained 4 heating zones, a metering pump and a spin pack assembly. The pellets were gravity fed into a chilled feeder section and introduced into the extruder's heated barrel (see Table 6). The heated and homogenized melted resin from the extruder was fed into a heated metering pump (melt pump), and from the melt pump the extruded resin was fed into the heated block and the spinneret assembly. The spinneret had 60 holes with a capillary diameter of 0.200 millimeters and a L/D ratio of 2:1. (The spinneret may also be configured in other alternative manners. For example, the spinneret can be configured with capillary diameters from 0.150 to 0.300 millimeters (6 mil to 12 mil) and 15, 120 and 240 holes, as well as higher and lower diameters and numbers of holes.). Processing temperature profile ranges from 35° C. to 290° C. were used with pressures ranging from 200 to 5,000 psi in the barrel and 200 to 5,000 psi in the spin pack. As the molten filaments exited the spin pack they passed through a heated chimney collar that was 6-12 inches long and ranged in temperature from 50° C. to 170° C., and then through an air quench box. The spin pack was suspended vertically above a yarn take-up roll at a distance sufficient to allow crystallization of the molten filaments and application of spin finish lubricant. A spin finish solution of 25% polyethylene glycol 400 (PEG400) in water was used to hold the filaments together to form a yarn bundle. The speed of the yarn take-up rolls (typically 3-18 meters per minute) was set in proportion to the flow rate of the molten filament to control the denier and to convey the as spun yarn bundle to a Leesona winder.

TABLE 6

| Extruder Temperature Profile for P4HB Yarn | |
| --- | --- |
| Chimney | 110° C. ± 60° C. |
| Spinneret | 230° C. ± 30° C. |
| Pump | 230° C. ± 30° C. |
| Block | 230° C. ± 30° C. |
| Zone 4 | 250° C. ± 40° C. |
| Zone 3 | 215° C. ± 40° C. |
| Zone 2 | 180° C. ± 50° C. |

TABLE 6-continued

| Extruder Temperature Profile for P4HB Yarn | |
| --- | --- |
| Zone 1 | 75° C. ± 40° C. |
| Feed Zone | Ambient temp. |

Example 2

Extrusion of P4HB Yarn Using a Split Stream

Molten yarn was extruded as described in Example 1, except that the spinneret holes were divided into two groups of 30 holes each with clear separation between the two groups to form dual spinning streams. For example, P4HB yarn extruded from a 60-hole spinneret was split into two 30-filament streams. Each spinning stream was guided to a separate spin finish applicator, and wound separately on a spool. The P4HB yarn was oriented using the conditions shown in Table 7, and had the properties shown in Table 8.

Example 3

Extrusion of P4HB Yarn Using a Quad-Split Stream

Molten yarn is extruded as described in Example 1, except that the spinneret holes were divided into four groups with clear separation between the four groups to form quad spinning streams. For example, P4HB yarn extruded from a 60-hole spinneret may be split into four 15-filament streams. Each spinning stream is guided to a separate spin finish applicator, and wound separately on a spool.

Example 4

Orientation to Yield High Tenacity P4HB Yarn

The spooled, as spun multifilament yarns, from Examples 1 and 2 were oriented on a series of cold and heated godet pairs and separator rolls. The spin finish was reactivated by rewetting the yarn bundle with pure water followed by drawing at ratios and temperatures shown in Table 7. The yarns were then spooled onto cores by a yarn winder. In this example, the multifilament fiber was subjected to a maximum draw ratio of 7.36 to 8.50, and then allowed to relax at a ratio of 0.801 to 0.927.

TABLE 7

| Orientation Settings to Yield High Tenacity P4HB Yarn | | | | | | |
| --- | --- | --- | --- | --- | --- | --- |
| Roll 1 | Roll 2 | Godet Pair 1 | Godet Pair 2 | Godet Pair 3 | Roll 3 | Winder |
| Ambient Temp. | Ambient Temp. | 80° C. ± 30 | 80° C. ± 30 | 85° C. ± 30 | Ambient Temp. | Ambient Temp. |
| Draw Ratio Range Between Stands | | | | | | |
| 3.462 to 5.000 | 1.627 to 2.333 | 1.008 to 1.053 | 0.976 to 1.027 | 0.935 to 1.097 | 0.801 to 0.942 | |

The tenacity of the 30-filament 150-denier P4HB yarn produced according to this method was 9.395±0.45 grams per denier, and the yarn had an elongation to break of approximately 20% as shown in Table 8. The tenacity of the 60-filament P4HB yarn produced according to this method was 9.626±0.45 grams per denier, and the yarn had an elongation to break of approximately 24% as shown in Table 8. The tenacity of the 15-filament P4HB yarn produced according to this method was 9.2±0.45 grams per denier, and the yarn had an elongation to break of approximately 16% as shown in Table 8.

TABLE 8

Mechanical Test Data for High Strength P4HB Yarn

| Filaments | Denier | Load (kgf) | Break elongation (%) | Tenacity (gpd) |
|---|---|---|---|---|
| 30 | 150 ± 10 | 1.450 ± 0.061 | 20.3 ± 3.3 | 9.395 ± 0.45 |
| 30 | 66 ± 10 | 0.541 ± 0.03 | 20.3 ± 3.3 | 8.2 ± 0.500 |
| 60 | 300 ± 10 | 2.801 ± 0.085 | 24.3 ± 2.5 | 9.626 ± 0.45 |
| 15 | 60 ± 10 | 0.551 ± 0.018 | 16.0 ± 0.7 | 9.2 ± 0.304 |

Example 5

In-Line Orientation of P4HB Yarn

The as spun 30-filament yarn from Example 2 (with or without reactivation of the spin finish by rewetting) is not spooled after extrusion, but instead it is directly guided in-line to orientation godets and then spooled. Orientation settings and mechanical test data are the same as those listed in Tables 7 and 8. The ratio of the yarn exit velocity to the take-up speed may, if desired, be varied to control the denier of the yarn. For example, the yarn take up velocity could be increased to 15 meters per minute, and slightly different orientation conditions used relative to those shown in Table 7.

Example 6

Orientation of P4HB Yarn with Heated Water

The spooled as spun 30-filament yarn from Example 2 is oriented exactly as in Example 2 except heat is applied to the yarn between the roll stands using a hot water bath, and orientation ratios may be adjusted.

Example 7

Orientation of P4HB Yarn with Heated Air

The spooled as spun 30-filament yarn from Example 2 is oriented exactly as in Example 2 except heat is applied to the yarn between the roll stands using hot air, and orientation ratios adjusted.

Example 8

Preparation of P4HB Multifilament Braided Sutures

Oriented 30-filament, 66 denier P4HB yarn, and oriented 15-filament, 60 denier P4HB yarn produced according to Example 4 and with properties shown in Table 8 were braided to form the braid constructions shown in Table 9. The mechanical properties of the high strength braided sutures, determined according to USP 24, are also shown in Table 9.

TABLE 9

Braid Construction and Properties of High Strength P4HB Sutures

| | Braid Construction | | | Mechanical Properties | |
|---|---|---|---|---|---|
| | | | | Tensile | Break |
| Lot Number | Core denier | Sheath denier | Pick Count | Diameter (mm) | Load (kgf) | Elong. (%) |
| USB290S | 2 × 150 | 16 × 150 | 52 ppi | 0.668 | 24.102 | 41.8 |
| 140356 | 4 × 150 | 16 × 150 | 39 ppi | 0.632 | 25.106 | 36.5 |
| 140361 | 5 × 150 | 16 × 150 | 39 ppi | 0.663 | 26.237 | 36.4 |
| 150024-1510 | 3 × 60 | 16 × 60 | 60 ppi | 0.390 | 9.300 | 30.8 |
| 150026-1510 | 4 × 60 | 16 × 60 | 60 ppi | 0.393 | 9.761 | 31.2 |
| 15002712 | 1 × 60 | 12 × 60 | 45 ppi | 0.302 | 6.597 | 27.0 |
| 15002512 | 1 × 60 | 8 × 60 | 45 ppi | 0.257 | 4.596 | 26.2 |

Example 9

Multifilament P4HB Axial Braided Sutures

The oriented 30-filament yarn produced in Example 4, with properties shown in Table 8, was braided with a construction in which the sheath carriers were augmented with straight members of yarn. The straight members (no braid angle) were braided into the sheath carriers (with a braid angle) to form a composite sheath construction.

Example 10

Multifilament P4HB Flat Braided Suture Tape

The oriented 30-filament yarn produced in Example 4, with properties shown in Table 8, was braided without a core using a 13-carrier braider. Each carrier was loaded with multiple yarns bundled together to vary the sheath denier, and increase the width and thickness of the flat braided suture. The constructions of the flat braided sutures and their properties are shown in Table 10. The flat braided sutures had widths ranging from 2.258 mm to 3.743 mm, and thicknesses ranging from 0.357 mm to 0.510 mm.

TABLE 10

Braid Constructions and Mechanical Properties of P4HB Flat Braided Sutures

| | Flat Braid Construction | | Mechanical Properties | |
|---|---|---|---|---|
| Lot Number | Sheath denier | Pick Count | Dimension (mm) | Tensile Load (N) | Break Elong. (%) |
| 140353 | 13 × 3 × 140 | 18 | 0.357 × 2.258 | 392 | 30.9 |
| 140354 | 13 × 6 × 120 | 17 | 0.486 × 3.094 | 620 | 33.9 |
| 140355 | 13 × 7 × 140 | 18 | 0.510 × 3.743 | 835 | 38.4 |

Example 11

Preparation of P4HB High Strength Monofilament by Melt Extrusion

Bulk P4HB resin in pellet form was dried to less than 300 ppm water using a rotary vane vacuum pump system. The dried resin was transferred to an extruder feed hopper with nitrogen purge to keep the pellets dry. The pellets were gravity fed into a chilled feeder section and introduced into the extruder barrel, which was 1.50 inches in diameter and fitted with an extrusion screw with a 30:1 L/D ratio. The extruder barrel contained 5 heating zones (or extrusion zones)—zones 1, 2, 3, 4 and 5, and was manufactured by American Kuhne. The heated and homogenized melted resin from the extruder was fed into a heated metering pump (melt pump) and from the melt pump the extruded resin was fed into the heated block and an eight-hole spinneret assembly with appropriately sized spinneret holes (e.g. 254 µm to 2,540 µm). Processing profile ranges from 40° C. to 260° C. for temperatures, and 400 psi to 2000 psi for pressures, were used. The molten filaments were water quenched (at a temperature of 5° C. to 30° C.), allowed time to crystallize, and then conveyed into a three-stage orientation, with inline relaxation, before winding of the monofilaments on spools. The orientation settings for each stage of orientation are shown in Table 11. In the first orientation stage, the filaments were oriented at ambient temperature (14-30° C.) with an orientation setting of 3.5-3.7 (see Table 11). In the second and third stages, the filaments were oriented using a hot water bath placed between the rollers of each stage with a set temperature of 93° C. and orientation ratio settings between 1.5 and 2.27 for the second stage, and 1.02 and 1.1 for the third stage (see Table 11.) After orientation, the P4HB monofilament fiber was relaxed by passing the fiber through a hot water bath set at 73° C. using orientation ratios of 1 to 1.03 as shown in Table 11.

TABLE 11

Orientation Settings to Prepare P4HB Monofilament Fiber

| Monofilament Size | Orientation Ratio Settings | | | |
|---|---|---|---|---|
| | First Stage | Second Stage | Third Stage | Relaxation |
| 8-0 | 3.6 | 1.5 | 1.02 | 1 |
| 6-0 | 3.6 | 1.84 | 1.04 | 1.03 |
| 5-0 | 3.7 | 1.95 | 1.02 | 1 |
| 3-0 | 3.6 | 2.06 | 1.04 | 1.02 |
| 0 | 3.5 | 2.2 | 1.06 | 1.03 |
| 1 | 3.5 | 2.27 | 1.1 | 1.03 |

The actual total draw ratio (measured from line speeds), fiber diameter, elongation to break and tensile strength (stress) were determined for each monofilament fiber size, and are shown in Table 12. The results shown in Table 11 demonstrate that P4HB monofilament fiber with tensile strength ranging from 1,090 to 1,282 MPa can be produced by initially cold drawing P4HB fiber extrudate that has been allowed time to crystallize, followed by hot drawing at a temperature above the melt temperature of the P4HB fiber.

TABLE 12

Properties of P4HB Monofilament Fiber Produced by Cold Drawing Followed by Hot Drawing

| Monofilament Size | Total Draw Ratio | Diameter (mm) | Elongation (%) | Tensile Strength (MPa) |
|---|---|---|---|---|
| 8-0 | 5.50 | 0.063 | 17.5 | 1,124 |
| 6-0 | 7.06 | 0.119 | 26.5 | 1,198 |
| 5-0 | 7.38 | 0.155 | 22.0 | 1,282 |
| 3-0 | 7.84 | 0.294 | 28.5 | 1,057 |
| 0 | 8.49 | 0.452 | 30.9 | 1,031 |
| 1 | 8.88 | 0.510 | 33.1 | 1,090 |

Example 12

Preparation of a Knitted Mesh from High Strength P4HB Monofilament

Spools with P4HB monofilament fiber (size 5/0) prepared using methods described in Example 11 were converted into P4HB monofilament mesh as follows: Monofilament fibers from 49 spools were mounted on a creel, aligned side by side and pulled under uniform tension to the upper surface of a "kiss" roller. The "kiss" roller was spun while semi-immersed in a bath filled with a 10% solution of Tween® 20 lubricant. The Tween® 20 lubricant was deposited on the surface of the sheet of fiber. Following the application of Tween® 20, the sheet of fiber was passed into a comb guide and then wound on a warp beam. A warp is a large wide cylinder onto which individual fibers are wound in parallel to provide a sheet of fibers. Next, warp beams were converted into a finished mesh fabric by means of interlocking knit loops. Eight warp beams were mounted in parallel onto tricot machine let-offs and fed into the knitting elements at a constant rate determined by the 'runner length'. Each individual monofilament fiber from each beam was fed through a series of dynamic tension elements down into the knitting 'guides'. Each fiber was passed through a single guide, which was fixed to a guide bar. The guide bar directed the fibers around the needles forming the mesh fabric structure. The mesh fabric was then pulled off the needles by the take down rollers at a constant rate of speed determined by the fabric 'quality'. The mesh fabric was then taken up and wound onto a roll and scored ultrasonically with water, heat set in hot water, and then washed with a 70% aqueous ethanol solution. The mesh had the following properties: a pore diameter of 500±100 µm, thickness of 0.5±0.2 mm, areal density of approx. 182±50 g/m$^2$, and a burst strength greater than 24.5 Kg.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A multifilament yarn or monofilament fiber comprising a 4-hydroxybutyrate polymer or copolymer
    wherein the yarn has a tenacity greater than 8.1 grams per denier but less than 12 grams per denier; and one or more properties selected from the group consisting of: an elongation to break of between 10% to 30%; and a denier per filament between 1.7 and 9.0, and
    wherein the monofilament fiber has a tensile strength between 800 MPa and 1,500 MPa and a minimum knot pull tensile strength greater than 0.25 kgf; and one or more properties selected from the group consisting of: a Young's Modulus of less than 2 GPa and an elongation to break of 15% to 120%.

2. A method for preparing the multifilament yarn or a monofilament fiber of claim 1, wherein the method comprises: (a) spinning a multifilament yarn or monofilament fiber comprising a 4-hydroxybutyrate polymer or copolymer, and (b) cold drawing the multifilament yarn or monofilament fiber, wherein the multifilament yarn or monofilament fiber is hot drawn after cold drawing at a temperature above the melt temperature of the polymer or copolymer, wherein the monofilament fiber is cold drawn with an orientation ratio of 3 to 4, and then hot drawn in one or more subsequent draws.

3. The method of claim 2, wherein the multifilament yarn is cold drawn with an orientation ratio of 2 to 6, and then hot drawn in one or more subsequent draws to yield a yarn with a tenacity of at least 8.1 grams per denier.

4. The method of claim 3, further comprising relaxing and/or annealing the fiber.

5. The method of claim 2, wherein the multifilament yarn or monofilament fiber are spun from a polymer or copolymer with a weight average molecular weight between 50 kDa and 1,200 kDa measured by gel permeation chromatography relative to polystyrene.

6. The method of claim 2, wherein the monofilament fiber has an elongation to break between 15% and 120%.

7. The multifilament yarn of claim 1, wherein the yarn has a tenacity greater than 10 grams per denier.

8. The multifilament yarn of claim 1, wherein the yarn has been oriented in a multi-stage orientation process, wherein the yarn is hot drawn in at least one stage.

9. The multifilament yarn of claim 8, wherein the yarn is cold drawn in the first stage of the multi-stage orientation process.

10. The multifilament yarn of claim 1, wherein the retained breaking load of the yarn decreases less than 65% after implantation for two weeks.

11. The multifilament yarn or monofilament fiber of claim 1, further comprising an additive wherein the additives are plasticizers, nucleants, compatibilizers, porogens, radiolabelled substances, imaging agents, radiopaque markers, contrast agents, dyes, bioactive agents, absorbable polymers, natural polymers, and synthetic polymers.

12. The multifilament yarn or monofilament fiber of claim 1, wherein the weight average molecular weight of the 4-hydroxybutyrate polymer or copolymer is between 50 kD and 1,200 kD.

13. The monofilament fiber of claim 1, wherein the fiber has been allowed time to crystallize before drawing.

14. The monofilament yarn of claim 1 wherein the yarn has been oriented in a multi-stage orientation process.

15. The multifilament yarn of claim 14, wherein the yarn is cold drawn in the first stage of the multi-stage orientation process.

16. The monofilament fiber of claim 1 wherein the monofilament fiber has been drawn at a temperature below 50° C., before being drawn at a temperature above the melt temperature of the fiber.

17. The multifilament yarn or monofilament fiber of claim 1 wherein the multifilament yarn or monofilament fiber is produced by a method comprising: (a) producing the polymer with a recombinant *E. coli* cell culture, (b) extracting and purifying the polymer from the biomass, (c) spinning the multifilament yarn or monofilament fiber from the polymer, (d) cold drawing the multifilament yarn or monofilament fiber, (e) hot drawing the multifilament yarn or monofilament fiber after cold drawing at a temperature above the melt temperature of the polymer or copolymer, and (f) optionally relaxing and/or annealing the multifilament yarn or monofilament fiber, wherein the multifilament yarn or monofilament fiber is biocompatible.

18. A medical device comprising the multifilament yarn or the monofilament fiber of claim 1, wherein the device is a suture, monofilament suture, multifilament suture, braided suture, hybrid suture of monofilament and multifilament fibers, barbed suture, self-retaining suture, braid, ligature, tape, knitted or woven mesh, non-woven mesh, knitted tube, monofilament mesh, multifilament mesh, patch, wound healing device, bandage, wound dressing, burn dressing, ulcer dressing, skin substitute, hemostat, tracheal reconstruction device, organ salvage device, dural substitute, dural patch, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, suture anchor, soft suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, stent, coronary stent, cardiovascular stent peripheral stent, ureteric stent, urethral stent, urology stent, gastroenterology stent, nasal stent, ocular stent, neurology stent, stent graft, cardiovascular patch, vascular closure device, intracardiac septal defect repair device, atrial septal defect repair device, PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, embolization device, anastomosis device, cell seeded device, controlled release device, drug delivery device, plastic surgery device, breast lift device, mastopexy device, breast reconstruction device, breast augmentation device, breast reduction device, devices for breast reconstruction following mastectomy with or without breast implants, facial reconstructive device, forehead lift device, brow lift device, eyelid lift device, face lift device, rhytidectomy device, thread lift device to lift and support sagging areas of the face, brow and neck, rhinoplasty device, device for malar augmentation, otoplasty device, neck lift device, mentoplasty device, cosmetic repair device, device for facial scar revision, and enclosures, pouches, holders, covers, clamshells, casings to hold implantable medical devices.

19. The device of claim 18, wherein the device is sterile and/or biocompatible.

20. The device of claim 18, wherein the device has been sterilized by ethylene oxide, electron beam irradiation or gamma irradiation and/or contains less than 20 endotoxin units.

21. The device of claim 20, wherein the device is a mesh produced by a method comprising: (a) knitting or weaving the monofilament fiber or multifilament yarn and (b) packaging and sterilizing the mesh.

22. The device of claim 21 wherein the mesh can withstand a burst pressure of at least 0.1 kPa.

23. The device of claim 18, wherein the device is a braid or tape with a breaking load greater than 1.0, 10.0, 20.0, 30.0, 40.0, 50.0, 60.0, 70.0 or 80.0 kgf.

24. The device of claim 18, wherein the device is a braid, with a diameter less than 0.8 mm, and a breaking load greater than 22 kgf, or a tape with a thickness less than 0.52 mm and a width less than 3.75 mm, and a breaking load greater than 35 kgf.

25. The medical device of claim 18 further comprising one or more of the following: plasticizer, nucleant, dye, medical marker, bioactive agent, therapeutic agent, antimicrobial agent, diagnostic agent, prophylactic agent, protein, peptide, antibody, polysaccharide, glycoprotein, lipid, lipoprotein, nucleic acid molecule, inorganic or organic synthetic molecule, contrast agent, radiopaque marker, radioactive substance, hyaluronic acid or derivative thereof, collagen, hydroxyapatite, synthetic polymer, natural polymer or one or more absorbable polymers derived from glycolic acid, glycolide, lactic acid, lactide, 1,4-dioxanone, trimethyl carbonate, ε-caprolactone.

26. The medical device of claim 25, wherein the antimicrobial agent is selected from one or more of the following: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes.

27. A method of using the device of claim 18 comprising implanting the device in the body of a patient in need thereof.

28. The method of claim 27, wherein the device is implanted using an open procedure, arthroscopic procedure, laparoscopic procedure, or delivered from a preconfigured delivery unit that may or may not be under tension.

29. The method of claim 27, wherein the device is a suture anchor, bone anchor, soft suture anchor, suture, tape, mesh or patch, and is preloaded for delivery.

30. The method of claim 27 wherein the device is used in orthopedic surgery, ligament and tendon repairs, Bankart lesion repair, SLAP lesion repair, acromion-clavicular repair, capsular shift/capsulolabral reconstruction, deltoid repair, Labral repair of the shoulder, Capsular/Labral Repairs of the Hip, rotator cuff tear repair, biceps tenodesis, foot and ankle medial/lateral repair and reconstruction, mid- and forefoot repair, Hallux valgus reconstruction, metatarsal ligament/tendon repair and reconstruction, Achilles tendon repair, ulnar or radial collateral ligament reconstruction, lateral epicondylitis repair, biceps tendon reattachment, knee extra-capsular repair, iliotibial band tenodesis, patellar tendon repair, vastus medialis obliquus (VMO) advancement, knee joint capsule closure, hand and wrist collateral ligament repair, scapholunate ligament reconstruction, tendon transfers in phalanx, volar plate reconstruction, acetabular labral repair, anterior ligament repair, spinal repair, fracture fixation, cardiovascular surgery, general surgery, gastric surgery, bowel surgery, abdominoplasty, plastic, cosmetic and reconstructive surgery, forehead lifting, brow lifting, eyelid lifting, facelift, neck lift, breast lift, lateral canthopexy, elevation of the nipple, breast reconstruction, breast reduction, breast augmentation, mastopexy, pelvic floor reconstruction, cystocele and rectocele repair, low anterior resection, urethral suspension, obstetrics and gynecological surgery, Nissen Fundoplication, myomectomy, hysterectomy, sacrolpopexy, cesarean delivery, hernia repair, general soft tissue approximation and ligation, wound closure reduction of wide scars, wound hernia repair, hemostasis, anastomosis, abdominal closure, laparoscopic procedures, partial nephrectomy, and implantation of cardiac rhythm management (CRM) devices, including pacemakers, defibrillators, generators, neurostimulators, ventricular access devices, infusion pumps, devices for delivery of medication and hydration solutions, intrathecal delivery systems, pain pumps, and other devices to provide drugs or electrical stimulation to a body part.

31. The multifilament yarn of claim 1, wherein the yarn has a denier per filament between 1.7 and 6.

32. The monofilament fiber of claim 16, wherein the monofilament fiber has been drawn at a temperature below 45° C. before being drawn at a temperature above the melt temperature of the fiber.

33. The device of claim 24, wherein the device is a braid, with a diameter less than 0.7 mm, and a breaking load greater than 24 kgf, or a tape with a thickness less than 0.52 mm and a width less than 3.75 mm, and a breaking load greater than 60 kgf.

34. The device of claim 33, wherein the tape has a breaking load of up to 80 kgf.

35. A multifilament yarn or monofilament fiber comprising a 4-hydroxybutyrate polymer or copolymer
wherein the yarn has one or more properties selected from the group consisting of: a tenacity greater than 8.1 grams per denier but less than 12 grams per denier; an elongation to break of between 10% to 30%; and a denier per filament between 1.7 and 9.0, and
wherein the monofilament fiber has one or more properties selected from the group consisting of: a tensile strength between 500 MPa and 1,500 MPa; a Young's Modulus of less than 2 GPa and an elongation to break of 15% to 120%,
wherein the multifilament yarn or monofilament fiber is produced by a method comprising (a) spinning a multifilament yarn or monofilament fiber comprising a 4-hydroxybutyrate polymer or copolymer, and (b) cold drawing the multifilament yarn or monofilament fiber, wherein the multifilament yarn or monofilament fiber is hot drawn after cold drawing at a temperature above the melt temperature of the polymer or copolymer, wherein the monofilament fiber is cold drawn with an orientation ratio of 3 to 4, and then hot drawn in one or more subsequent draws.

36. The monofilament of claim 35, wherein the tensile strength is between 900 MPa and 1,500 MPa.

37. The monofilament or multifilament of claim 1, comprising a 4-hydroxybutyrate homopolymer.

38. The monofilament or multifilament of claim 1, wherein the fiber is spun from a polymer with a weight average molecular weight between 100 kDa and 1,200 kDa measured by gel permeation chromatography relative to polystyrene.

* * * * *